US010061039B2

(12) United States Patent
Kawanabe et al.

(10) Patent No.: US 10,061,039 B2
(45) Date of Patent: Aug. 28, 2018

(54) RADIATION IMAGING APPARATUS, RADIATION IMAGING SYSTEM, METHOD FOR FABRICATING RADIATION IMAGING APPARATUS

(71) Applicant: CANON KABUSHIKI KAISHA, Tokyo (JP)

(72) Inventors: Jun Kawanabe, Kawasaki (JP); Minoru Watanabe, Yokohama (JP); Keigo Yokoyama, Honjo (JP); Masato Ofuji, Takasaki (JP); Kazuya Furumoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/359,169

(22) Filed: Nov. 22, 2016

(65) Prior Publication Data

US 2017/0153336 A1 Jun. 1, 2017

(30) Foreign Application Priority Data

Nov. 26, 2015 (JP) .................................. 2015-230695

(51) Int. Cl.
| | |
|---|---|
| *G01T 1/24* | (2006.01) |
| *A61B 6/00* | (2006.01) |
| *H04N 5/378* | (2011.01) |
| *H04N 5/32* | (2006.01) |
| *H01L 27/146* | (2006.01) |

(52) U.S. Cl.
CPC ................ *G01T 1/247* (2013.01); *A61B 6/52* (2013.01); *H01L 27/14612* (2013.01); *H01L 27/14641* (2013.01); *H01L 27/14663* (2013.01); *H04N 5/32* (2013.01); *H04N 5/378* (2013.01); *A61B 6/4233* (2013.01)

(58) Field of Classification Search
CPC ......... A61B 6/4233; A61B 6/52; G01T 1/247; H01L 27/14612; H01L 27/14641; H01L 27/14663; H04N 5/32; H04N 5/378
See application file for complete search history.

(56) References Cited

U.S. PATENT DOCUMENTS

2005/0151863 A1* 7/2005 Johannesson .......... G01B 11/04
348/294
2011/0121189 A1* 5/2011 Okada ............... H01L 27/14663
250/370.08
(Continued)

FOREIGN PATENT DOCUMENTS

JP 2011-174908 A 9/2011

*Primary Examiner* — Mark R Gaworecki
(74) *Attorney, Agent, or Firm* — Canon U.S.A., Inc. IP Division

(57) ABSTRACT

An apparatus includes a plurality of first groups having same configurations and arranged in a row direction and a column direction, each of the first groups including a plurality of pixels for obtaining a radiation image and at least one detection section for detecting an amount of incident radiation, and a plurality of detection signal lines connected to the plurality of detection sections. Two of the plurality of first groups which are arranged in the column direction are shifted from each other in the row direction, and the detection sections included in the two groups are connected to different detection signal lines in the plurality of detection signal lines.

19 Claims, 17 Drawing Sheets

(56) References Cited

U.S. PATENT DOCUMENTS

| | | | | |
|---|---|---|---|---|
| 2011/0174957 A1* | 7/2011 | Okada | ............... | H01L 27/14603 250/208.1 |
| 2014/0339561 A1* | 11/2014 | Yokoyama | ........ | H01L 31/02240 257/53 |
| 2016/0178763 A1* | 6/2016 | Okada | ............... | H01L 27/14605 250/370.09 |

* cited by examiner

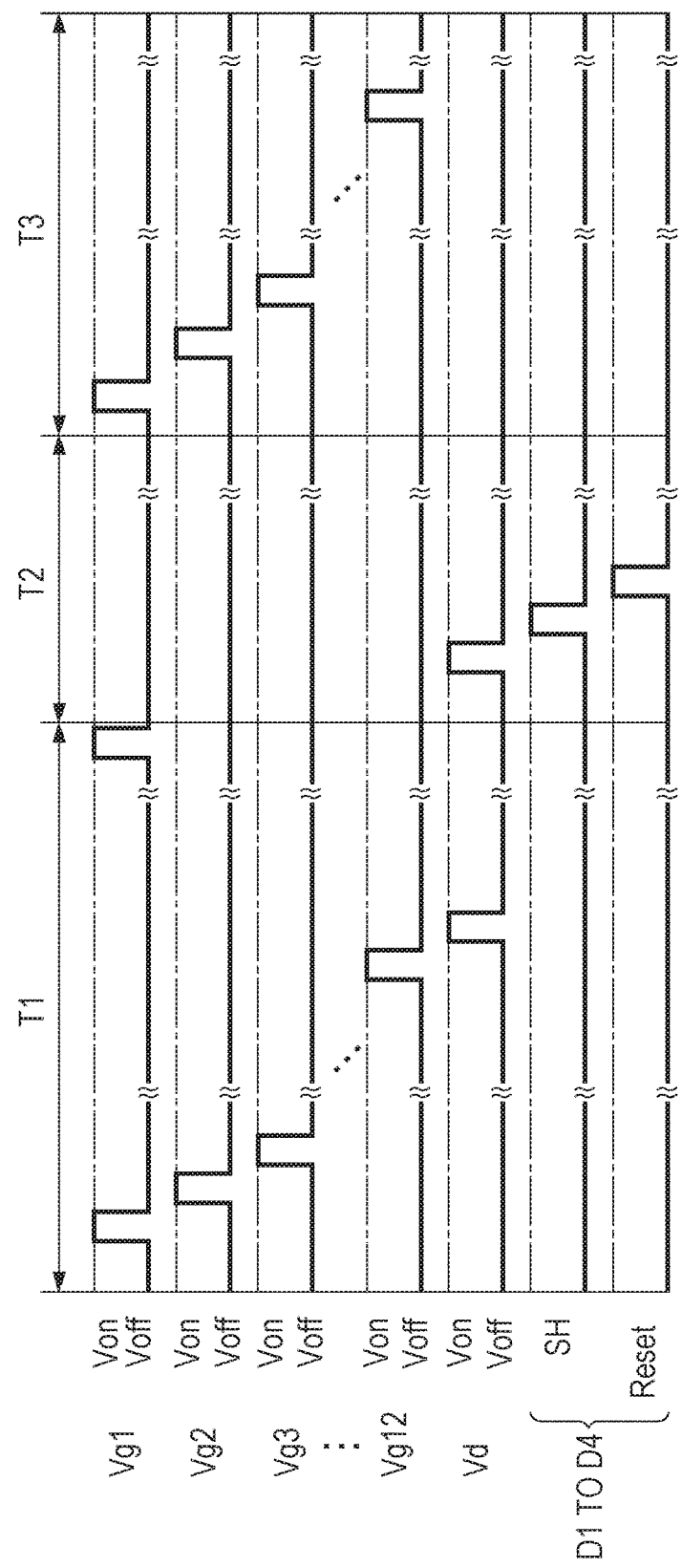

RADIATION IMAGING APPARATUS, RADIATION IMAGING SYSTEM, METHOD FOR FABRICATING RADIATION IMAGING APPARATUS

BACKGROUND OF THE INVENTION

Field of the Invention

The aspect of the embodiments relates to a radiation imaging apparatus, a radiation imaging system, and a method for fabricating the radiation imaging apparatus.

Description of the Related Art

Radiation imaging apparatuses having a pixel array including pixels arranged in a two dimensional array have been widely used. Each of the pixels includes a combination of a conversion element which converts radiation into charge and a switch element, such as a thin-film transistor (TFT). Such a radiation imaging apparatus generally has an automatic exposure control (AEC) function. The AEC function detects an amount of radiation incident on the radiation imaging apparatus during irradiation with radiation. Japanese Patent Laid-Open No. 2011-174908 discloses a technique of dividing an imaging region which is larger than an exposure range of a photomask when a pixel array including detection pixels used to detect a radiation amount is formed and exposing individual divided regions.

In the method disclosed in Japanese Patent Laid-Open No. 2011-174908, in a case where regions including the detection pixels are formed in a matrix by repeatedly using one mask pattern, reading lines used to read signals from the detection pixels are shared by a plurality of detection pixels included in a plurality of regions arranged along the reading lines. To detect radiation amounts in the plurality of regions arranged along the reading lines, the signals of the detection pixels are to be successively read for individual regions, and therefore, a reading rate for the detection of the radiation amount may be deteriorated.

SUMMARY OF THE INVENTION

According to an embodiment, an apparatus includes a plurality of first groups having same configurations configured to be arranged in a row direction and a column direction, each of the first groups including a plurality of pixels for obtaining a radiation image and at least one detection section for detecting an amount of incident radiation, a plurality of detection signal lines configured to connect to detection sections of the plurality of first groups, and a second group having a plurality of pixels for obtaining a radiation image and configured differently from each of the plurality of first groups. The second group is arranged in the row direction of one of two of the first groups which are arranged in the column direction, and the two groups are shifted from each other in the row direction in accordance with a width of the second group in the row direction. The detection sections included in the two groups are connected to different detection signal lines in the plurality of detection signal lines.

Further features of the aspect of the embodiments will become apparent from the following description of exemplary embodiments with reference to the attached drawings.

BRIEF DESCRIPTION OF THE DRAWINGS

FIG. 7 is a timing chart illustrating an operation of the radiation imaging apparatus of FIG. 1.

DESCRIPTION OF THE EMBODIMENTS

Figure 1:
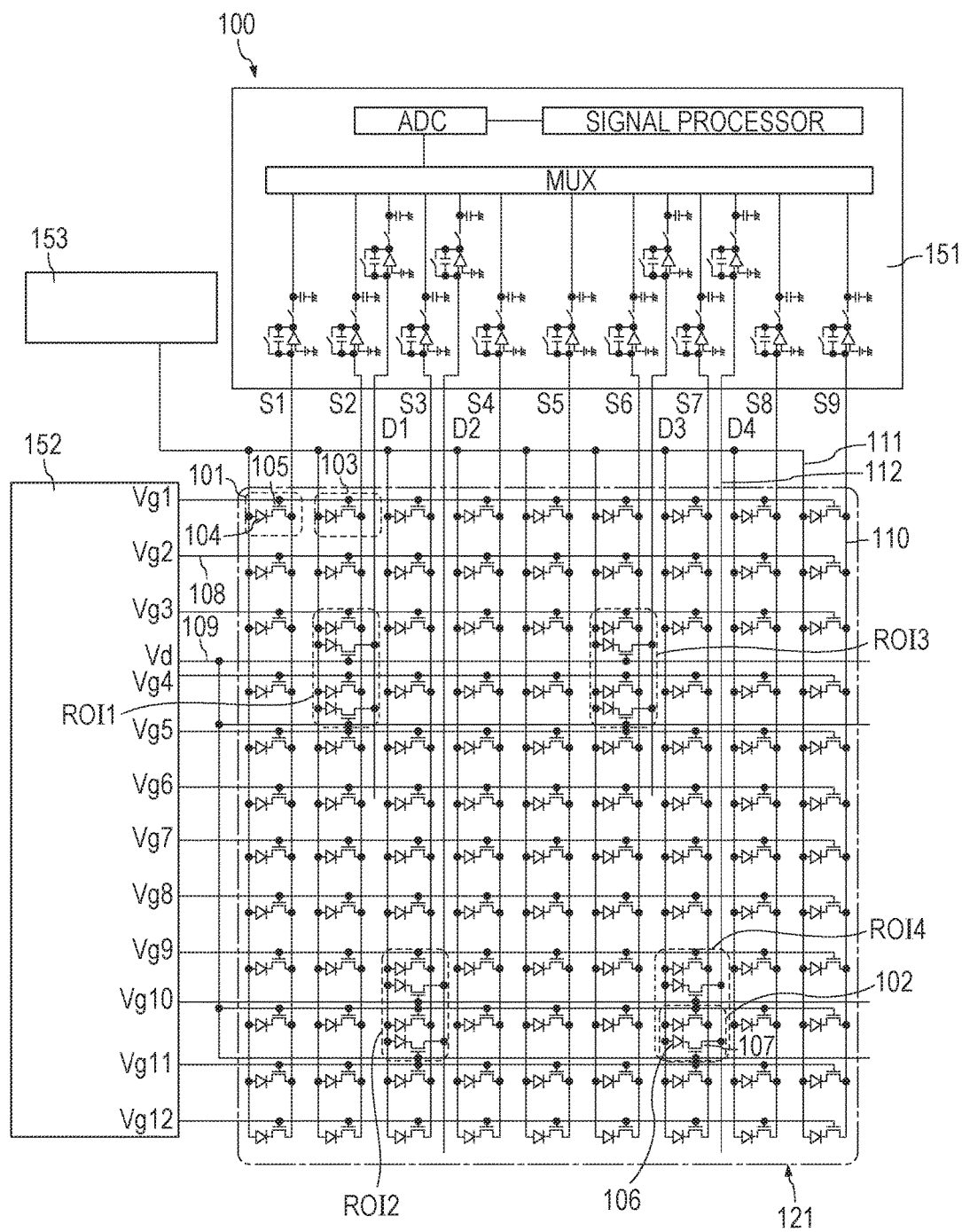
FIG. 1 is an equivalent circuit diagram illustrating a circuit configuration of a radiation imaging apparatus according to a first embodiment.

Hereinafter, exemplary embodiments of a radiation imaging apparatus will be described with reference to the accompanying drawings. Note that, in the description and the drawings below, common components in a plurality of drawings are denoted by common reference numerals. Therefore, the common components are described with reference to one another in the plurality of drawings, and redundant descriptions of the components having the common reference numerals are appropriately omitted. Note that radiation of the aspect of the embodiments may include, in addition to beams generated by particles (including photons) emitted due to radioactive decay, such as α rays, β rays, and γ rays, beams having energy which is the same level as the beams generated by particles, such as X rays, particle rays, and cosmic rays.

First Embodiment

A radiation imaging apparatus according to a first embodiment will be described with reference to FIGS. 1 to 7. FIG. 1 is an equivalent circuit diagram illustrating a circuit configuration of a radiation imaging apparatus 100 according to a first embodiment. The radiation imaging apparatus 100 includes an imaging region 121 including a plurality of pixels 101 and 103 used to capture a radiation image and a plurality of pixels 102 used to detect an amount of incident radiation during irradiation, a reading unit 151, a controller 152, and a bias power source 153. Although an example of arrangement of pixels in a matrix of 12 rows by 9 columns is illustrated in FIG. 1, the aspect of the embodiments is not limited to this, and arrangement of pixels in a matrix of 1000 rows by 1000 columns may be employed or arrangement of pixels in a matrix of 5000 rows by 5000 columns may be employed. Note that, in this specification, a direction in which image signal lines 110 and detection signal lines 112 which transfer signals output from the pixels 101 to 103 to the reading unit 151 extend is referred to as a "column direction" and a direction intersecting with the column direction is referred to as a "row direction". The row direction and the column direction may be orthogonal to each other.

Each of the pixels 101 and 103 includes a conversion element 104 which converts incident radiation or incident light into a signal corresponding to an amount of the incident radiation or the incident light so as to obtain a radiation image and a switch element 105 which outputs the signal generated by the conversion element 104 to a corresponding one of the image signal lines 110. The conversion element 104 may be an indirect conversion element including a scintillator which converts radiation into light and a photoelectric conversion element which converts the light obtained by the conversion through the scintillator into charge, for example. As the conversion element 104, a direct conversion element which directly converts radiation into charge may be used, for example. As the switch element 105, a thin-film transistor (TFT) using amorphous silicon or polycrystalline silicon, for example, may be used. For example, the polycrystalline silicon may be used depending on a characteristic required for the TFT. However, a semiconductor material used for the TFT is not limited to silicon but another semiconductor material, such as germanium or a compound semiconductor, may be used.

Each of the pixels 102 includes a conversion element 106 which converts incident radiation or incident light into a signal corresponding to an amount of incident radiation or incident light so as to detect an amount of incident radiation during irradiation and a switch element 107 which outputs the signal generated by the conversion element 106 to a corresponding one of the detection signal lines 112. Furthermore, each of the pixels 102 may include the conversion element 104 and the switch element 105 which are used to obtain a radiation image. The conversion element 106 and the switch element 107 may have configurations the same as those of the conversion element 104 and the switch element 105, respectively.

The reading unit 151 receives signals generated by the individual conversion elements 104 through the switch elements 105 and the image signal lines 110 (S1 to S9). Furthermore, the reading unit 151 receives signals generated by the individual conversion element 106 through the switch elements 107 and the detection signal lines 112 (D1 to D4). The reading unit 151 includes operation amplifiers, a multiplexer, an AD converter, and a signal processor. In the reading unit 151, the image signal lines 110 and the detection signal lines 112 are individually connected to inversion input terminals of the operation amplifiers. Furthermore, the inversion input terminals of the operation amplifiers are connected to output terminals through feedback capacitances, and non-inversion input terminals are connected to arbitrary fixed potentials. The operation amplifiers function as charge/voltage conversion circuits. In a following stage of the operation amplifiers, the AD converter is connected through sample-and-hold circuits and the multiplexer. The reading unit 151 constitutes a digital conversion circuit which converts the signals generated by the conversion elements 104 and the conversion elements 106 into digital electric signals through the image signal lines 110 and the detection signal lines 112. The signal processor may externally output the converted digital electric signals as signals for a radiation image or may generate a radiation image using the digital electric signals converted by the signal processor, for example. Furthermore, the signal processor may externally transmit a signal corresponding to an amount of radiation detected by the pixels 102 so as to control irradiation. The reading unit 151 may integrate the various circuits including the operation amplifiers, the multiplexer, the AD converter, and the signal processor or the reading units 151 may be individually disposed for the circuits.

A controller 152 transmits signals Vg (signals Vg1 to Vg12 in the configuration of FIG. 1) to the switch elements 105 in the corresponding rows through control lines 108 extending in the row direction so as to control the switch elements 105. Furthermore, the controller 152 transmits a signal Vd to the switch elements 107 through a control line 109 extending in the row direction so as to control the switch elements 107. The bias power source 153 supplies a common bias voltage to the pixels 101, 102, and 103 through bias lines 111.

The radiation imaging apparatus 100 illustrated in FIG. 1 includes detection sections ROI (region of interest) for detection of an amount of incident radiation, that is, four detection sections ROI1 to ROI4 surrounded by dotted lines. Each of the detection sections ROI includes at least one conversion element 106 (the pixel 102). Furthermore, in a case where a plurality of conversion elements 106 are included in one detection section ROI, the individual conversion elements 106 are connected to the same detection signal line 112. In this embodiment, each of the detection sections ROI includes two conversion elements 106 (two pixels 102). Furthermore, the two conversion elements 106 included in the detection section ROI1 are connected to the same detection signal line 112 (D1) through the corresponding switch elements 107. Similarly, the conversion elements 106 included in the detection section ROI2 are connected to one of the detection signal lines 112 (D2), the conversion elements 106 included in the detection section ROI3 are connected to one of the detection signal lines 112 (D3), and the conversion elements 106 included in the detection section ROI4 are connected to one of the detection signal lines 112 (D4). Although the detection sections ROI are disposed in four positions in a matrix of 2 rows by 2 columns in the imaging region 121 of the radiation imaging apparatus 100 in this embodiment, the detection sections ROI may be disposed in 25 positions in a matrix of 5 rows by 5 columns or 100 positions in a matrix of 10 rows by 10 columns, for example. The number of detection sections ROI is appropriately determined in accordance with a configuration of the radiation imaging apparatus 100. The detection sections ROI may be evenly disposed in the imaging region 121 or unevenly disposed such that the detection sections ROI are concentrated on a particular region. Furthermore, although the two pixels 102 are arranged in the column direction in each of the detection sections ROI in this embodiment, the disclosure is not limited to this. The number of pixels 102 may be 1 or may be 3 or more. Furthermore, a plurality of pixels 102 may be arranged in the row direction in each of the detection sections ROI, and the conversion elements 106 included in each of the detection sections ROI may be connected to the same detection signal lines 112. Furthermore, the pixels 102 included in each of the detection sections ROI may be consecutively arranged as illustrated in FIG. 1, or one to a several number of pixels 101 or pixels 103 may be arranged between the pixels 102.

In this embodiment, the conversion elements 106 included in different detection sections ROI are connected to different detection signal lines 112. Accordingly, signals of the conversion elements 106 in the plurality of detection sections ROI may be simultaneously read, and an operation of detecting a radiation amount may be performed at high speed. A timing of the operation of detecting a radiation amount will be described later.

Figure 2A:
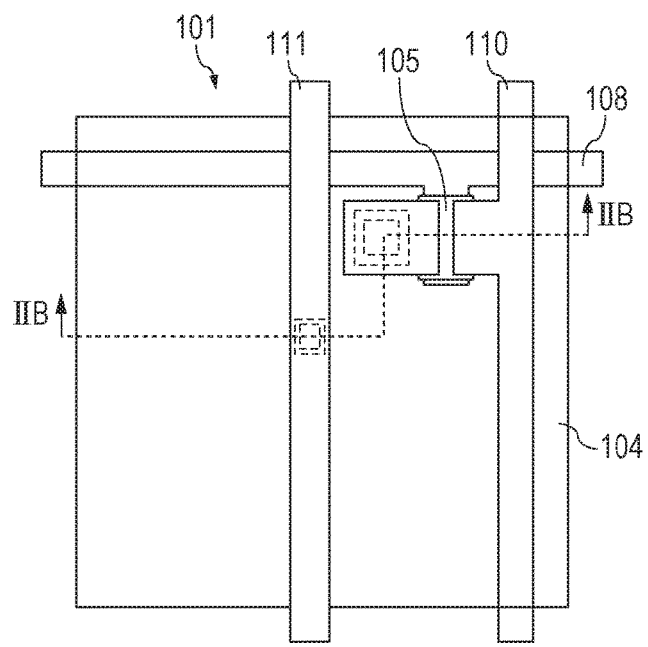
FIGS. 2A and 2B are a plan view and a cross-sectional view, respectively, of a pixel for imaging a radiation image included in the radiation imaging apparatus of FIG. 1.
Figure 2B:
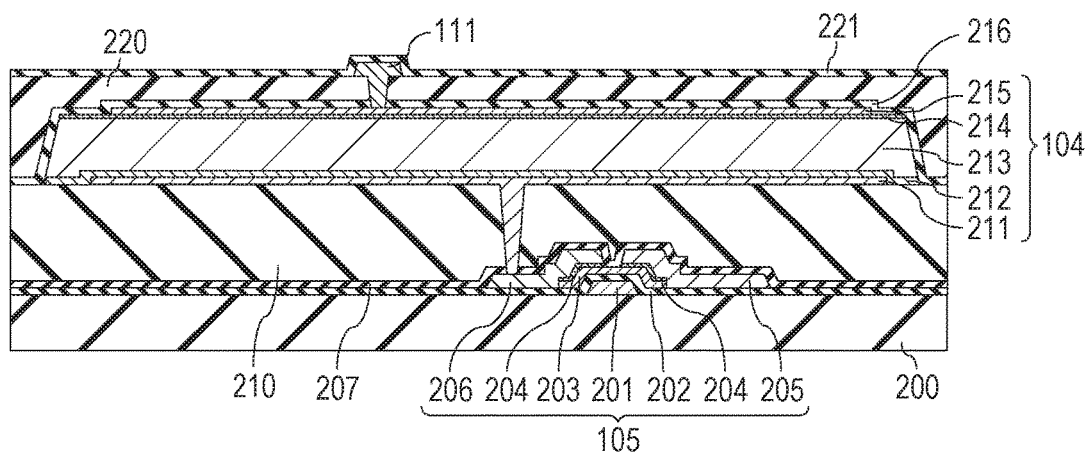

Next, a configuration of the pixel 101 will be described with reference to FIGS. 2A and 2B. FIG. 2A is a plan view of the pixel 101, and FIG. 2B is a cross sectional view taken along a dotted line IIB to IIB of FIG. 2A. As described above, the pixel 101 includes the conversion element 104 and the switch element 105 which outputs a signal generated by the conversion element 104 when being selected by the signal Vg supplied from the controller 152 through a corresponding one of the control lines 108. The conversion element 104 illustrated in FIGS. 2A and 2B is an indirect conversion element using a scintillator which converts radiation into light and a photoelectric conversion element which converts the light obtained by the conversion through the scintillator into charge, for example. The conversion element 104 is disposed on the switch element 105 through an interlayer insulating layer 210. The switch element 105 is disposed on an insulating substrate 200, such as a glass substrate. The switch element 105 includes a control electrode 201, an insulating layer 202 functioning as a gate insulating film, a semiconductor layer 203, a high-concentration layer 204 constituted by a semiconductor having impurity concentration higher than that of the semiconductor layer 203, a first main electrode 205, and a second main electrode 206 which are laminated on the substrate 200. The high-concentration layer 204 has a portion which is in contact with the first main electrode 205 and a portion which is in contact with the second main electrode 206, and a region in the semiconductor layer 203 positioned between the first main electrode 205 and the second main electrode 206 serves as a channel region of the switch element 105. The control electrode 201 is electrically connected to a corresponding one of the control lines 108, the first main electrode 205 is electrically connected to a corresponding one of the image signal lines 110, the second main electrode 206 is electrically connected to an individual electrode 211 provided for each conversion element 104. In this embodiment, the first main electrode 205, the second main electrode 206, and the image signal line 110 are formed of the same conductive layer when the switch element 105 is formed, and the first main electrode 205 serves as part of a corresponding one of the image signal lines 110. An insulating layer 207 and the interlayer insulating layer 210 are disposed on the switch element 105.

Although a case where an inversely-staggered TFT using the semiconductor layer 203 mainly formed of amorphous silicon and the high-concentration layer 204 is used as the switch element 105 is illustrated in FIG. 2B, the aspect of the embodiments is not limited to this. A staggered TFT mainly formed of crystalline silicon may be used as the switch element 105, for example, or an organic TFT, an oxide TFT may be used. The interlayer insulating layer 210 covers the switch element 105 and has a contact hole in a position between the second main electrode 206 and the individual electrode 211. The individual electrode 211 and the second main electrode 206 of the conversion element 104 are electrically connected to each other through the contact hole formed in the interlayer insulating layer 210. The conversion element 104 includes the individual electrode 211, a high concentration layer 212, a semiconductor layer 213, a high concentration layer 214, and a common electrode 215 which receives a bias voltage which is commonly applied to the pixels from the bias power source 153 which are laminated in this order on the interlayer insulating layer 210 from a side near the interlayer insulating layer 210. In this embodiment, the high concentration layers 212 and 214 are semiconductor layers having different conductive types and form a PIN-type photoelectric conversion element with the semiconductor layer 213. A type of the photoelectric conversion element is not limited to the PIN type, and a MIS-type photoelectric conversion element may be used. An insulating layer 216 covers the conversion element 104, and furthermore, an interlayer insulating layer 220 is disposed on the insulating layer 216. The common electrode 215 of the conversion element 104 is electrically connected to a corresponding one of the bias lines 111 disposed on the interlayer insulating layer 220. An insulating layer 221 serving as a protection film is disposed on the interlayer insulating layer 220 and the corresponding one of the bias lines 111. A scintillator (not illustrated) is disposed on the insulating layer 221 and converts incident radiation into light. The conversion element 104 converts the light generated by the scintillator into a signal corresponding to an amount of light.

Figure 3A:
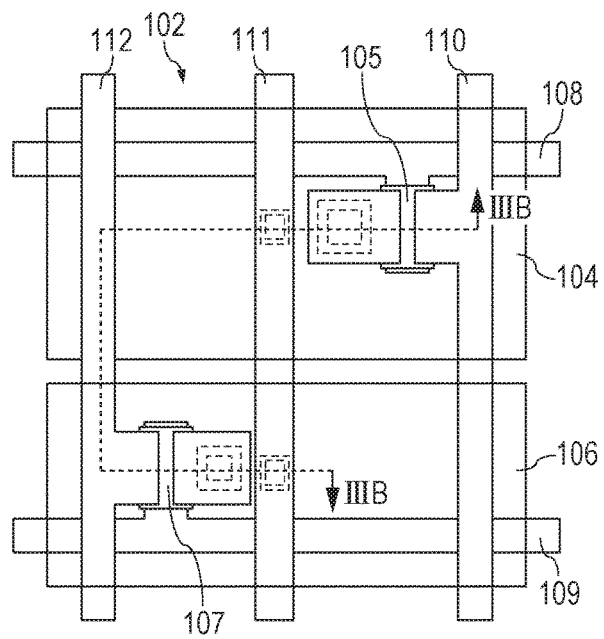
FIGS. 3A and 3B are a plan view and a cross-sectional view, respectively, of a pixel for detecting a radiation amount included in the radiation imaging apparatus of FIG. 1.
Figure 3B:
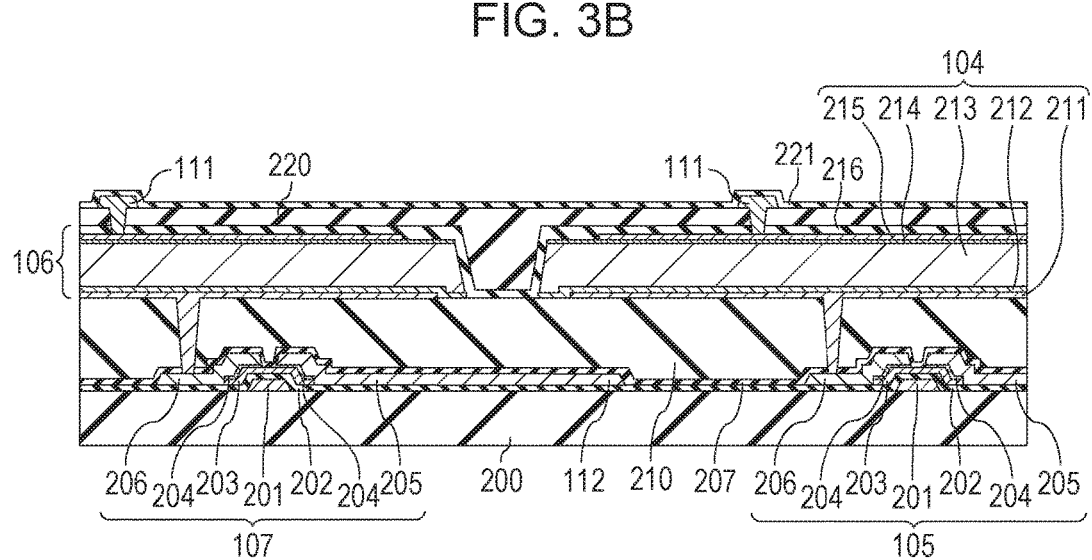

FIGS. 3A and 3B are diagrams illustrating a configuration of the pixels 102. FIG. 3A is a plan view of the pixel 102, and FIG. 3B is a cross sectional view taken along a dotted line IIIB to IIIB of FIG. 3A. The pixel 102 includes the conversion element 106 and the switch element 107 which outputs a signal generated by the conversion element 106 when being selected by the signal Vd supplied from the controller 152 through a corresponding one of the control lines 109. In this embodiment, the pixels 102 includes the conversion element 104 and the switch element 105 which are used to perform imaging of a radiation image and the conversion element 106 and the switch element 107 which are used to detect an amount of incident radiation. The switch element 107 on the substrate 200 has a configuration the same as that of the switch element 105 included in the pixel 101. The conversion element 106 on the interlayer insulating layer 210 has a configuration the same as that of the conversion element 104 included in the pixel 101. The common electrode 215 of the conversion element 104 and the conversion element 106 is electrically connected to a corresponding one of the bias lines 111 disposed on the interlayer insulating layer 220. An individual electrode 211 of the conversion element 106 is connected to a second main electrode 206 of the conversion element 106 through a contact hole formed in an interlayer insulating layer 210. A first main electrode 205 of the conversion element 106 is connected to a corresponding one of the detection signal lines 112. An insulating layer 207 and an interlayer insulating layer 210 are disposed on the detection signal lines 112. Configurations other than those described above may be the same as those of the pixel 101 described above.

As described in FIGS. 2A and 2B and FIGS. 3A and 3B, sizes of the conversion elements 104 in the pixels 101 and 102 are different from each other in this embodiment. Therefore, even in a case where amounts of radiation incident on the pixels 101 and 102 are the same, charge amounts corresponding to signals output from the corresponding conversion elements 104 are different from each other. In a case where electric signals read by the reading unit 151 from signals output from the conversion elements 104 of the pixels 102 are used for a radiation image, appropriate correction, such as white correction (gain correction), may be performed. The correction may be performed using values of the pixels 101 and 103 arranged adjacent to or in the vicinity of the pixels 102, for example.

Figure 4A:
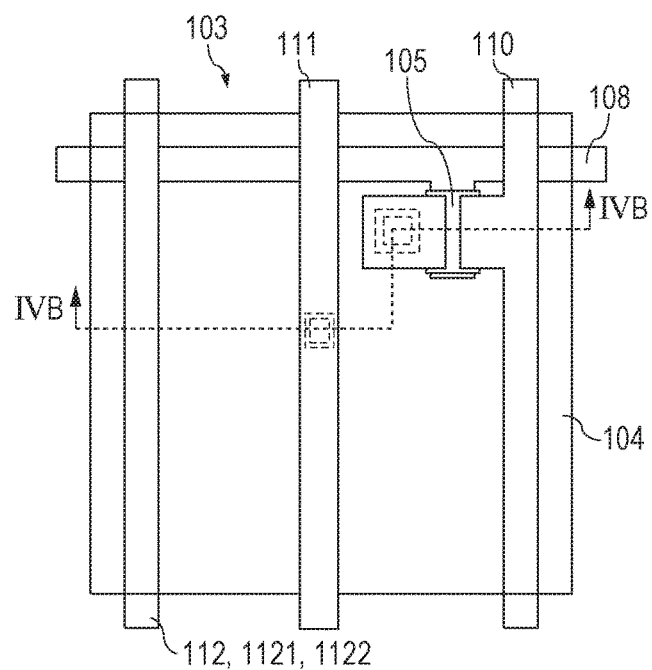
FIGS. 4A and 4B are a plan view and a cross-sectional view, respectively, of a pixel for imaging a radiation image which passes a detection signal line included in the radiation imaging apparatus of FIG. 1.
Figure 4B:
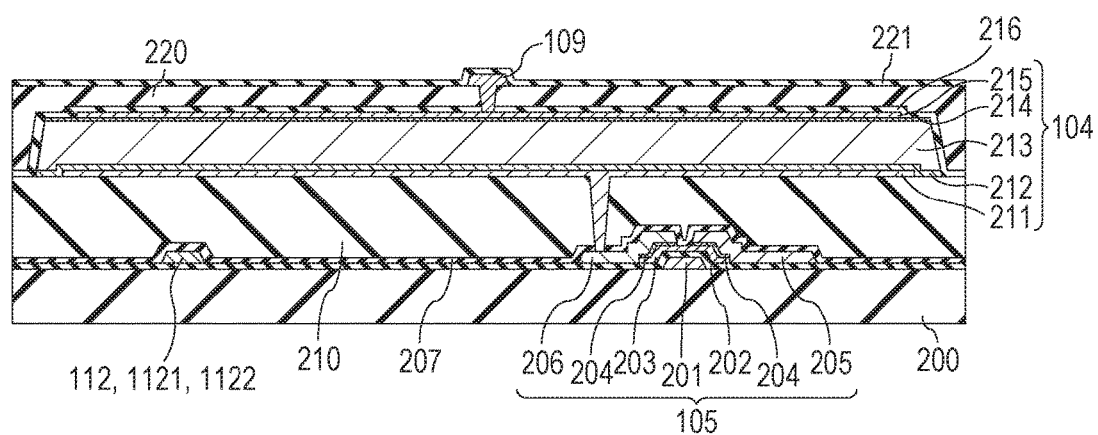

FIGS. 4A and 4B are diagrams illustrating a configuration of the pixel 103. FIG. 4A is a plan view of the pixel 103, and FIG. 4B is a cross sectional view taken along a dotted line IVB to IVB of FIG. 4A. According to this embodiment, when compared with the pixel 103 with the pixel 101, a corresponding one of the detection signal lines 112, a signal line 1121 described below, or a dummy signal line 1122 is arranged in the pixel 103 and passes below the individual electrode 211 of the conversion element 104. Configurations other than those described above may be the same as those of the pixel 101.

Figure 5:
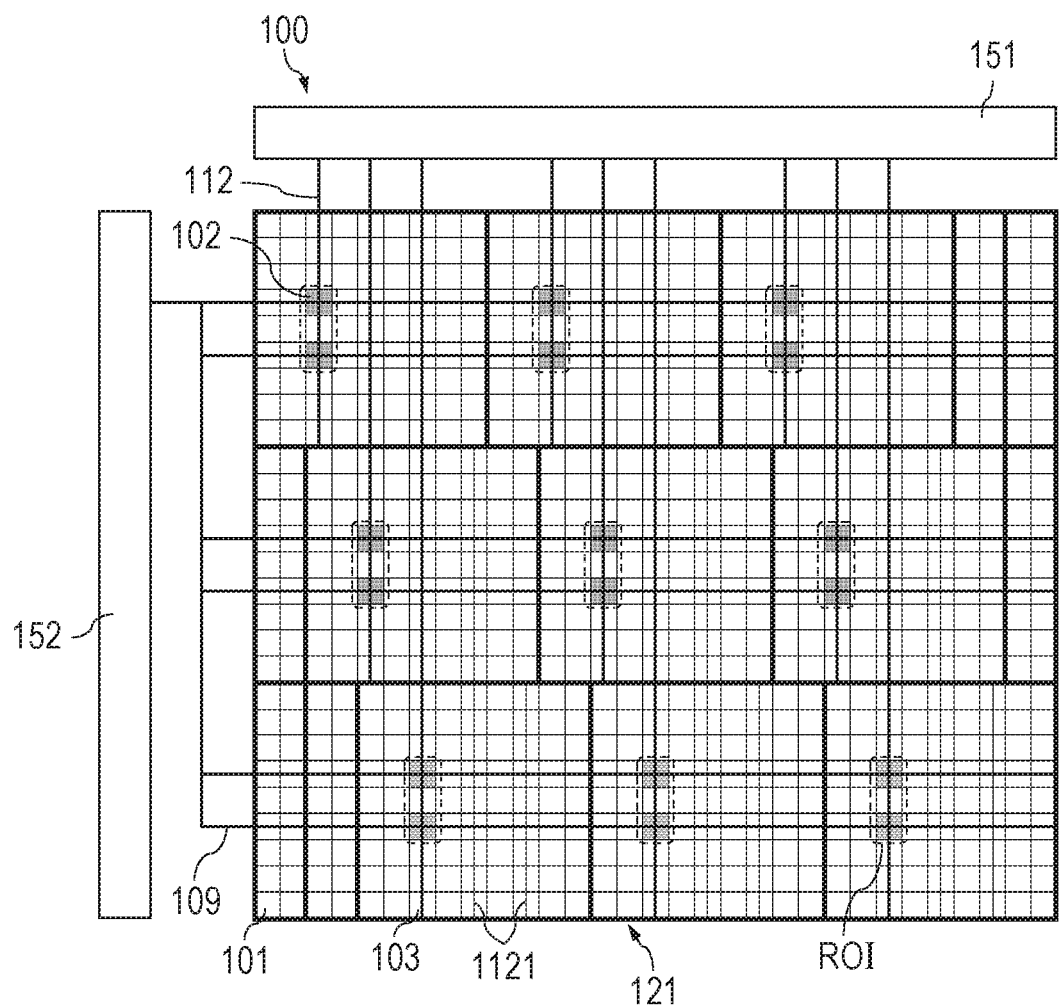
FIG. 5 is a diagram schematically illustrating layout of a configuration of the radiation imaging apparatus of FIG. 1.

FIG. 5 is a diagram schematically illustrating layout of a configuration of the radiation imaging apparatus 100 according to this embodiment. In FIG. 5, the pixels 101, 102, and 103 which are disposed in the imaging region 121, the detection signal lines 112, the control lines 109, the detection sections ROI, the reading unit 151, and the controller 152 in the circuit configuration illustrated in FIG. 1 are illustrated, and the image signal lines 110 and the control lines 108 are omitted for simplicity of the drawing. In FIG. 5, the detection sections ROI each of which includes the two pixels 102 each of which includes the conversion element 106 are arranged in nine portions, and in each of the detection sections ROI, the single pixel 103 is disposed between the two pixels 102. Furthermore, the pixels 102 in the detection sections ROI which are arranged adjacent to each other in the column direction are connected to different detection signal lines 112. Accordingly, signals of the conversion elements 106 of the pixels 102 in the different detection sections ROI may be simultaneously read, and an operation of detecting a radiation amount may be performed at high speed. Furthermore, pixels including the detection sections ROI arranged in the imaging region 121 are periodically arranged in the row direction.

Figure 6A:
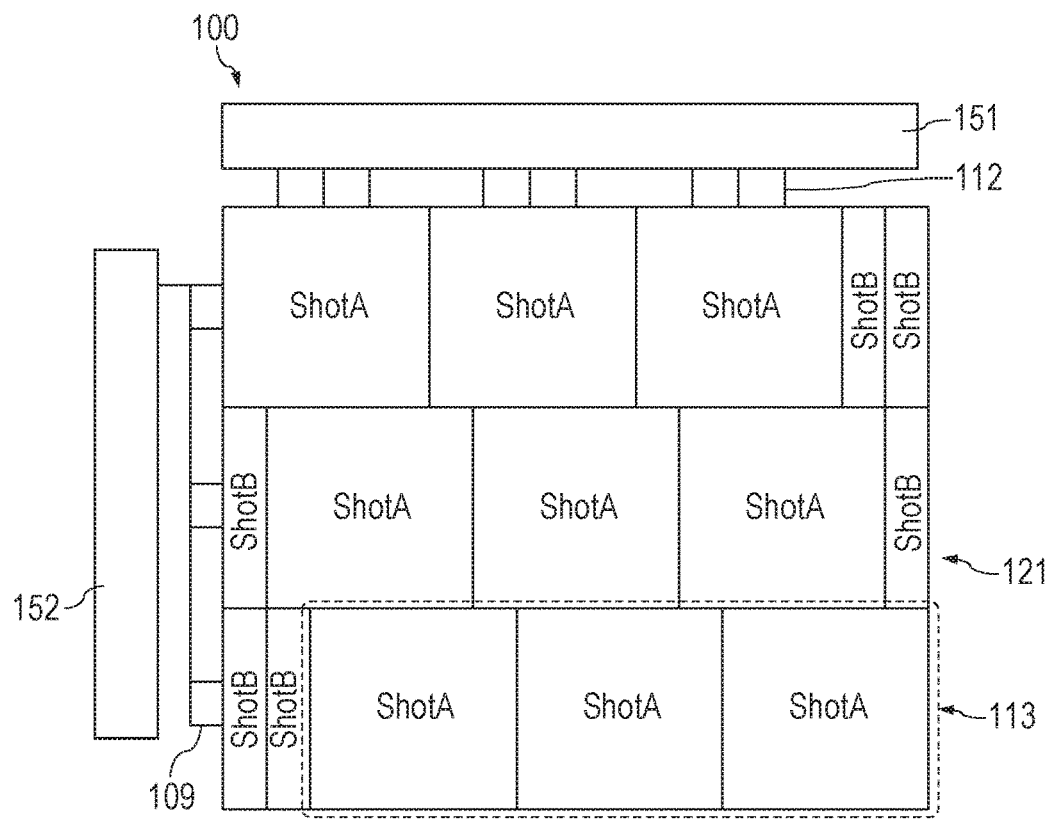
FIGS. 6A to 6C are diagrams illustrating an exposure region of the radiation imaging apparatus of FIG. 1.
Figure 6B:
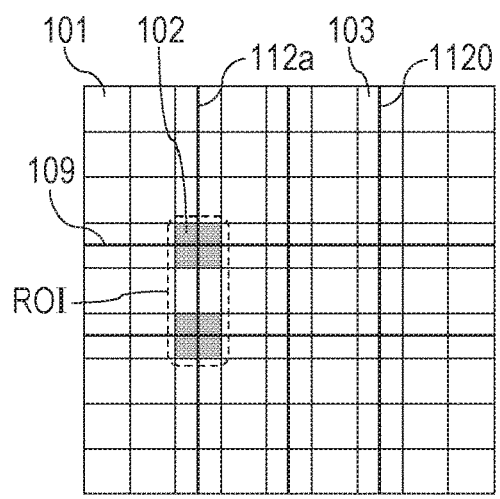
Figure 6C:
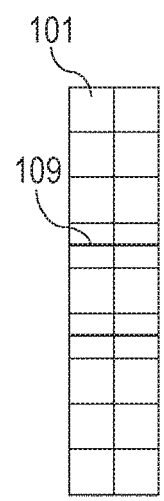

Next, a method for forming the imaging region 121 illustrated in FIG. 5 will be described with reference to FIGS. 6A to 6C. In a case where the imaging region 121 including the pixels 101, 102, and 103 is larger than a region formed by integrated exposure using one photomask, the imaging region 121 is divided into regions, and exposure is repeatedly performed on the individual regions. In FIG. 6A, the regions which are obtained by dividing the imaging region 121 and which are to be repeatedly exposed are illustrated. The imaging region 121 includes exposure regions ShotA formed when exposure is performed using the same mask pattern group and exposure regions ShotB formed when exposure is performed using the same mask pattern group which is different from the mask pattern group of the exposure region ShotA. Therefore, components formed in the exposure regions ShotA correspondingly have the same configurations, and similarly, components formed in the exposure regions ShotB correspondingly have the same configurations. In this embodiment, an exposure region group 113 which is a first group is formed by arranging three exposure regions ShotA each of which forms a sub-group in the row direction, and three exposure region groups 113 are arranged in the column direction. Therefore, the exposure region groups 113 serving as the first groups have the same configuration. Furthermore, the six exposure regions ShotB serving as second groups are arranged. The components included in each of the exposure regions ShotA include, as illustrated in FIG. 6B, the pixels 101, 102, and 103, a detection signal line 112a which is part of a corresponding one of the detection signal lines 112 and which is connected to the pixels 102 of a corresponding one of the detection sections ROI, and the control lines 109. Furthermore, the components included in each of the exposure regions ShotA include a signal line 1120 which is connected to a detection signal line 112a of other one of the exposure regions ShotA or which is part of the signal line 1121 described below. Furthermore, the components included in each of the exposure regions ShotB include, as illustrated in FIG. 6C, the pixels 101 and the control lines 109. Any of the detection sections ROI including the pixels 102 are not included in the exposure regions ShotB. As with the case of FIG. 5, the image signal lines 110 and the control lines 108 are omitted also in FIGS. 6A to 6C for simplicity of the drawings.

The exposure region ShotB is arranged adjacent to at least one of opposite ends of each of the exposure region groups 113 in the row direction. In this embodiment, two exposure regions ShotB are continuously arranged in the row direction so as to be adjacent to one of the opposite ends of the exposure region groups 113 disposed in an uppermost portion and a lowermost portion in the three exposure region groups 113 arranged in the column direction. One of the three exposure region groups 113 which is arranged in a middle portion has one exposure region ShotB at the opposite ends thereof. Therefore, the adjacent two of the exposure region groups 113 in the three exposure region groups 113 are shifted from each other in the row direction by a width of one exposure region ShotB in the row direction. An amount of the shift may correspond to a width of one exposure region ShotB as illustrated in FIG. 6A. Alternatively, the numbers of exposure regions ShotB arranged in one ends of the adjacent exposure region groups 113 may be different from each other by 2 or more. In this case, an amount of the shift of the adjacent exposure region groups 113 in the row direction is integer multiple of the width of one exposure region ShotB in the row direction. The amount of shift in the row direction between the adjacent exposure region groups 113 arranged in the column direction is determined such that the detection sections ROI arranged in the adjacent exposure region groups 113 are connected to different detection signal lines 112.

According to this embodiment, the detection signal lines 112 connected to the pixels 102 are arranged every two pixels in the row direction as illustrated in FIG. 5. Furthermore, the exposure region groups 113 which are adjacent to each other in the column direction are shifted from each other in the row direction as illustrated in FIG. 6A using the exposure regions ShotB by an interval between the detection signal lines 112. By this, as illustrated in FIG. 5, the pixels 102 of the detection sections ROI included in the exposure region groups 113 which are arranged adjacent to each other in the column direction are connected to different detection signal lines 112. Specifically, in two of the exposure region groups 113 which are adjacent to each other, the detection signal line 112 connected to the detection section ROI of one of the exposure region groups 113 is not connected to the detection signal line 112 connected to the detection section ROI of the other of the exposure region groups 113. Furthermore, as illustrated in FIGS. 5 and FIGS. 6A to 6C, similarly to the case of the exposure region groups 113 which are adjacent to each other in the column direction, the detection sections ROI which are disposed in different exposure region groups 113 may be connected to different detection signal lines 112.

If the exposure regions ShotA are arranged without shifting the exposure region groups 113 from one another in the row direction, the detection sections ROI arranged in the column direction are connected to the same detection signal line 112. Therefore, in the detection sections ROI arranged in the column direction, the switch elements 107 are to be successively operated and signals are to be successively read from the conversion elements 106. On the other hand, by shifting the exposure region groups 113 from one another in the row direction according to this embodiment, the detection sections ROI arranged in the column direction are connected to the different detection signal lines 112 and signals may be simultaneously read. In other words, signals generated by the conversion elements 106 of the pixels 102 in the different detection sections ROI may be simultaneously read. Accordingly, when a radiation image is captured while repeatability of pattern is realized for formation of pixels by exposing a pixel region, an operation of detecting an amount of radiation incident on the radiation imaging apparatus 100 may be performed at high speed.

Although the width of the exposure regions ShotB in the row direction and the interval between the detection signal lines 112 are the same as each other in this embodiment, the configuration of the exposure regions ShotB is not limited to this. The width of the exposure regions ShotB may be half of the interval between the detection signal lines 112. Although the exposure regions ShotB has the width corresponding to two pixels in the row direction in FIG. 6C, the exposure regions ShotB may have a width corresponding to one pixel. The configuration of the exposure regions ShotB is appropriately determined such that the pixels 102 in the different detection sections ROI may be simultaneously read by shifting the exposure regions ShotA arranged in the column direction by a predetermined width in the row direction.

Furthermore, as illustrated in FIG. 5, the signal lines 1121 are discontinued in the imaging region 121 without being connected to the detection sections ROI and the reading unit 151 in this embodiment. This is because, when the exposure regions ShotA are formed, the imaging region 121 is repeatedly exposed using a mask pattern group having a requisite minimum number of detection signal lines 112a and a requisite minimum number of signal lines 1120 arranged thereon. Therefore, although the detection signal lines 112 are arranged at even intervals in each of the exposure regions ShotA in the formed imaging region 121, the detection signal lines 112 are not arranged at even intervals in each of the exposure region groups 113. If the discontinued signal lines 1121 is an issue in the operation of the radiation imaging apparatus 100, layout of the exposure regions ShotA may be changed such that all the signal lines are connected to the reading unit 151, for example. This layout will be described in a second embodiment below.

Figure 17:
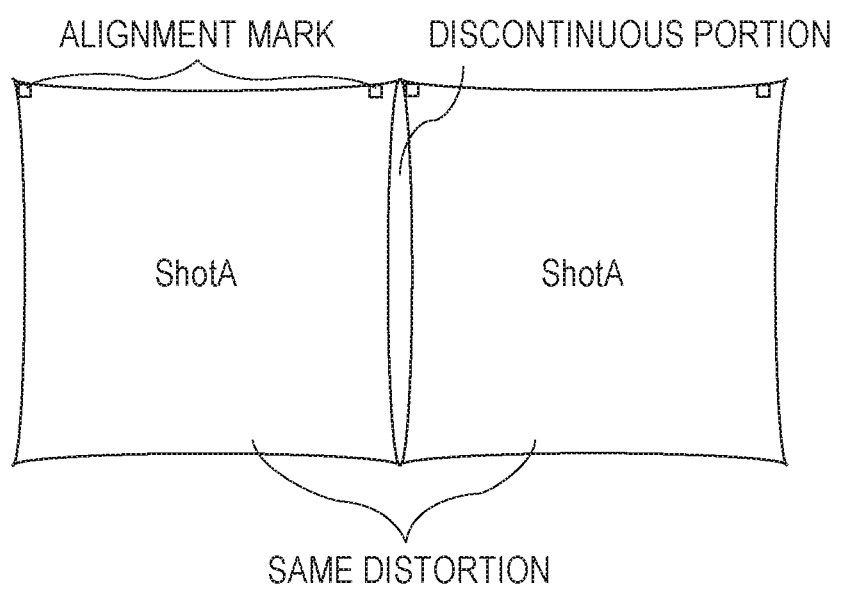
FIG. 17 is a diagram illustrating distortion caused by exposure in a process of forming a radiation imaging apparatus according to the aspect of the embodiments.

In this embodiment, different mask pattern groups are provided for the exposure regions ShotA and the exposure regions ShotB to fabricate the radiation imaging apparatus 100 and an operation of forming the imaging region 121 on the substrate is performed. By repeatedly performing exposure in the row direction and the column direction using the individual mask patterns, the plurality of exposure regions ShotA and the plurality of exposure regions ShotB are formed. For example, an operation of forming an exposure region ShotA is repeatedly performed in the row direction so that an exposure region group 113 having a plurality of exposure regions ShotA is formed. Thereafter, a plurality of exposure region groups 113 may be repeatedly formed in the column direction so that a region in which the exposure regions ShotA are arranged is formed in the imaging region 121. Therefore, the components included in each of the exposure regions ShotA have the same distortion caused by exposure in the formation process for individual exposure regions ShotA. Similarly, the components included in each of the exposure regions ShotB have the same distortion caused by exposure in the formation process for individual exposure regions ShotB. For example, as illustrated in FIG. 17, the individual exposure regions ShotA are distorted in the same direction and have the same evaluation value of the distortion. Furthermore, depending on the distortion or accuracy of alignment for each exposure, a discontinuous portion may be generated in a portion between the adjacent exposure regions ShotA and a portion between the adjacent exposure regions ShotB. Furthermore, components used to form exposure regions, such as alignment marks, may be periodically arranged for individual exposure regions ShotA and the individual exposure regions ShotB in the imaging region 121, for example.

Next, an operation of the radiation imaging apparatus 100 in this embodiment will be described with reference to a timing chart of FIG. 7. In a description below, signals Vg1 to Vgm (the signal Vgm corresponds to the Vg12 of FIG. 1, for example) are supplied to the control lines 108 which drive the pixels 101, and the signal Vd is supplied to the control lines 109 which drive the pixels 102. The switch elements 105 and 107 are brought into a conductive state when levels of signals supplied from the control lines 108 and 109 to gate electrodes of the switch elements 105 and 107 are in a high level, and brought into a non-conductive state when the levels of the signals supplied to the gate electrodes are in a low level. A combination of the signal level and the conductive state may be determined in accordance with a combination of a circuit configuration and a conductive type of the switch element. In FIG. 7, the high level is denoted by "Von" and the low level is denoted by "Voff".

First, a period T1 will be described. In the period T1, start of irradiation with radiation is waited. In this embodiment, the radiation imaging apparatus 100 is powered, imaging of a radiation image becomes available, an exposure switch of a radiation source is operated, and the irradiation with radiation is detected in the period T1. In the period T1, a signal Von is successively applied to the switch elements 105 and the switch elements 107, and the individual electrodes 211 of the conversion elements 104 and the conversion elements 106 are reset to potentials of the image signal lines 110 and the detection signal lines 112. The signal Von may be constantly applied to the switch elements 107. By this operation, charge caused by dark current is prevented from being accumulated in the conversion elements 104 and the conversion elements 106 for a long period of time. Although a length of the period T1 varies depending on an imaging method or an imaging condition, the length of the period T1 may be several seconds to several minutes.

Next, a period T2 will be described. During the period T2, the radiation imaging apparatus 100 is irradiated with radiation. The period T2 is started when start of the irradiation with radiation is detected and terminated when an exposure amount of radiation reaches an optimum radiation amount. In the period T2, an amount of radiation emitted to the radiation imaging apparatus 100 is monitored. In the period T2, the signal Von is applied as the signal Vd, and the switch elements 107 in the pixels 102 are intermittently brought into a conductive state. Since a signal Voff is constantly applied to the signals Vg1 to Vgm, the switch elements 105 are brought into a non-conductive state. Subsequently, in the detection signal lines 112 (D1 to D4), sample-and-hold SH is performed in the sample-and-hold circuits included in the reading unit 151 when the period in which the signal Von is applied to the switch elements 107 is terminated. Thereafter, charge of the detection signal lines 112 is reset (Reset). By this control, the reading unit 151 may read required signals with high accuracy while charge generated due to parasitic capacitance is suppressed in the signals of the conversion elements 106. Thereafter, when the amount of radiation emitted to the radiation imaging apparatus 100 which is read by the reading unit 151 reaches a setting value, the signal processor of the reading unit 151 may externally transmit a signal so as to control the irradiation with radiation.

Next, a period T3 will be described. In the period T3, after the irradiation with the radiation is terminated, the charge generated and accumulated in the pixels 101 due to the irradiation with the radiation is read as a signal. In the period T3, the signal Voff is applied as the signal Vd. Furthermore, the detection signal lines 112 may be connected to a fixed potential so that the detection signal lines 112 are prevented from being in a floating state. Furthermore, the signal Von is successively applied as the signals Vg1 to Vgm for scanning on the control lines 108, and signals accumulated in the conversion elements 104 of the individual pixels are transferred through the image signal lines 110 to the reading unit 151. Thereafter, a radiation image may be formed using the signals supplied from the conversion elements 104.

Although the conversion elements 106 are connected to the detection signal lines 112 through the switch elements 107 in this embodiment, the disclosure is not limited to this. The conversion elements 106 may be directly connected to the detection signal lines 112, for example. In this case, the control lines 109 are not required, and therefore, the circuit configuration of the imaging region 121 may be simplified, and a load of the control by the controller 152 may be reduced. Furthermore, intersection portions of the control lines 109 with the image signal lines 110 and the detection signal lines 112 are removed, and therefore, wiring capacitances of the image signal lines 110 and the detection signal lines 112 may be reduced.

Second Embodiment

Figure 8:
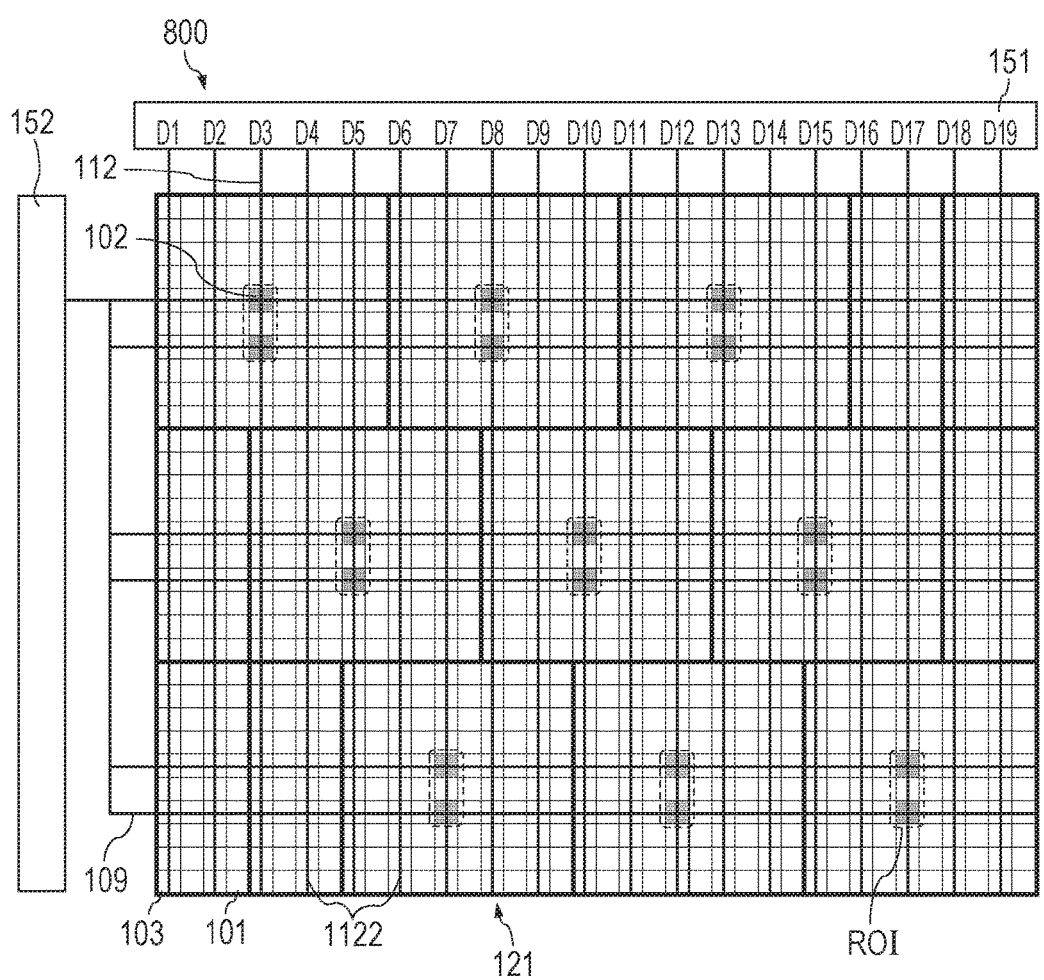
FIG. 8 is a diagram schematically illustrating a configuration of a radiation imaging apparatus according to a second embodiment.

A radiation imaging apparatus according to a second embodiment will be described with reference to FIG. 8 and FIGS. 9A to 9C. FIG. 8 is a diagram schematically illustrating layout of a configuration of a radiation imaging apparatus 800 according to the second embodiment. Also in FIG. 8, in the circuit configuration illustrated in FIG. 1, pixels 101, 102, and 103 which are disposed in an imaging region 121, detection signal lines 112, control lines 109, detection sections ROI, a reading unit 151, and a controller 152 are illustrated, and image signal lines 110 and control lines 108 are omitted for simplicity of the drawing. Unlike the radiation imaging apparatus 100 according to the first embodiment described above, the signal lines 1121 which are discontinued in the imaging region 121 and which are not connected to the reading unit 151 do not exist in this embodiment. However, dummy signal lines 1122 which are connected to the reading unit 151 but not connected to the pixels 102 of the detection sections ROI are arranged. Furthermore, arrangement of components formed in exposure regions ShotA and exposure regions ShotB are different from those in the radiation imaging apparatus 100 of the first embodiment described above. Configurations other than those described above may be the same as those of the radiation imaging apparatus 100. Also in this embodiment, the pixels 102 in the detection sections ROI which are arranged adjacent to each other in the row direction are connected to different detection signal lines 112.

Figure 9A:
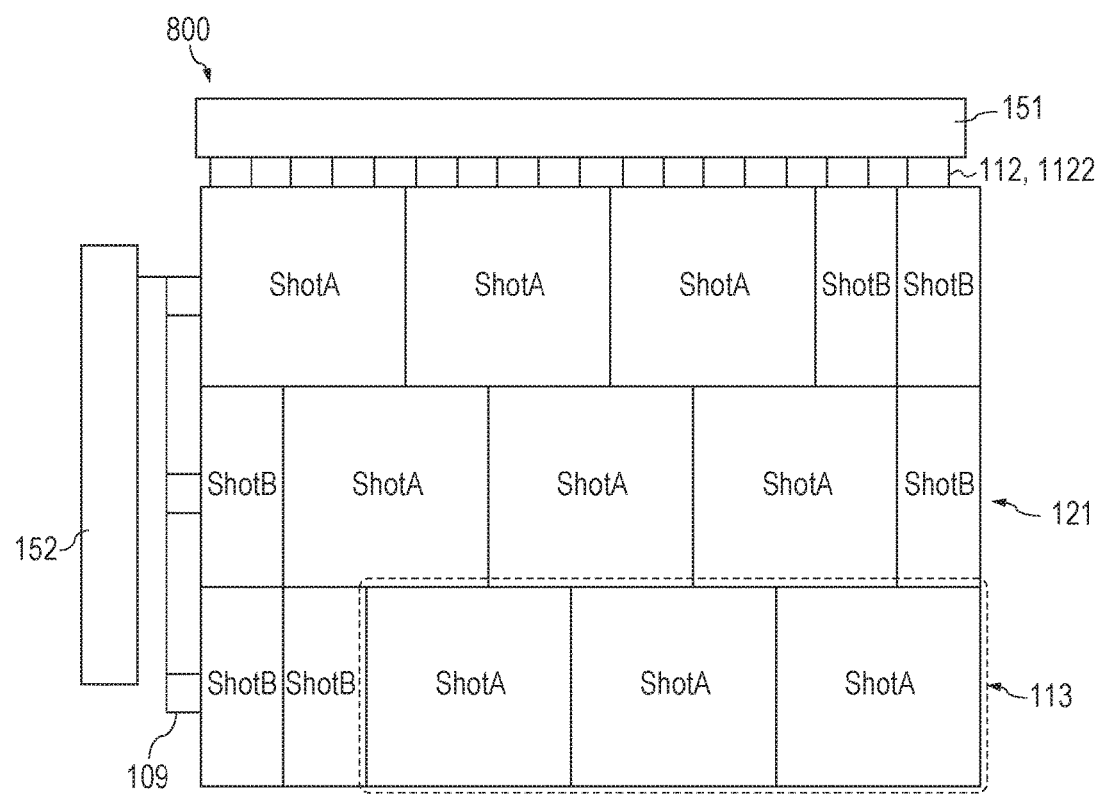
FIGS. 9A to 9C are diagrams illustrating an exposure region of the radiation imaging apparatus of FIG. 8.
Figure 9B:
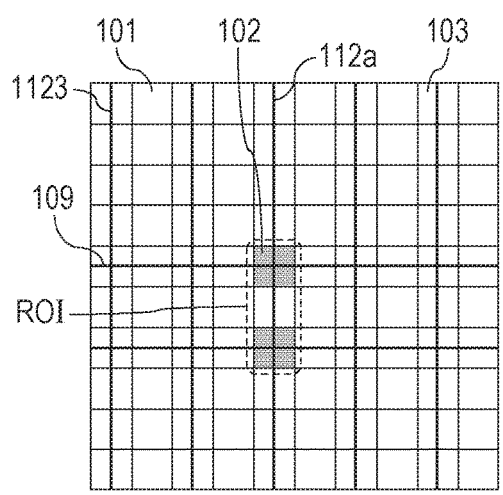
Figure 9C:
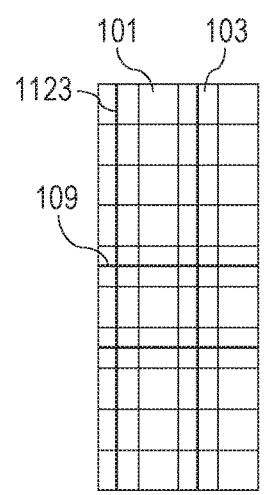

Next, a method for forming the imaging region 121 illustrated in FIG. 8 will be described with reference to FIGS. 9A to 9C. As illustrated in FIG. 9A, the imaging region 121 includes a plurality of exposure regions ShotA formed by exposure using the same mask pattern group. The imaging region 121 further includes a plurality of exposure regions ShotB formed by exposure using the same mask pattern which is different from that of the exposure regions ShotA. Therefore, components formed in the exposure regions ShotA correspondingly have the same configurations, and similarly, components formed in the exposure regions ShotB correspondingly have the same configurations. In this embodiment, an exposure region group 113 is formed by arranging three exposure regions ShotA in the row direction, and three exposure region groups 113 are arranged in the column direction. Therefore, the exposure region groups 113 have the same configuration. Furthermore, the six exposure regions ShotB are arranged. The components included in each of the exposure regions ShotA include, as illustrated in FIG. 9B, the pixels 101, 102, and 103, a detection signal line 112a which is part of a corresponding one of the detection signal lines 112 and which is connected to the pixels 102 of a corresponding one of the detection sections ROI, and the control lines 109. Furthermore, the components included in each of the exposure regions ShotA include a signal line 1123 which is connected to a detection signal line 112a of other one of the exposure regions ShotA and which is part of one of the dummy signal lines 1122. The components included in each of the exposure regions ShotB include, as illustrated in FIG. 9C, the pixels 101, the control line 109, and the signal lines 1123. Also in this embodiment, any of the detection sections ROI including the pixels 102 are not included in the exposure regions ShotB. The image signal lines 110 and the control lines 108 are omitted also in FIGS. 9A to 9C for simplicity of the drawings.

In this embodiment, the detection signal lines 112 and the dummy signal lines 1122 which extend in the column direction are arranged every two pixels in a row direction as illustrated in FIG. 8. Furthermore, the exposure region groups 113 which are adjacent to each other in the column direction are shifted from each other in the row direction as illustrated in FIG. 9A by twice the interval between the detection signal lines 112 and the dummy signal lines 1122 using the exposure regions ShotB. A shift amount of the exposure region groups 113 which are adjacent to each other in the column direction in the row direction is not limited to twice the interval between the detection signal lines 112, and may be the same as the interval or three or more times the interval. By this, the pixels 102 of the detection sections ROI included in the exposure region groups 113 which are arranged adjacent to each other in the column direction are connected to different detection signal lines 112. Furthermore, also in this embodiment, similarly to the case of the exposure region groups 113 which are adjacent to each other in the column direction, the detection sections ROI which are disposed in different exposure region groups 113 are connected to different detection signal lines 112. Accordingly, even in this embodiment, when a radiation image is captured while repeatability of pattern is realized for formation of pixels by exposing a pixel image, an operation of detecting an amount of radiation incident on the radiation imaging apparatus 800 may be performed at high speed.

Here, in this embodiment, the formed imaging region 121 includes the dummy signal lines 1122 (D1, D2, D4, D6, D9, D11, D14, D16, D18, and D19) which are not connected to the pixels 102 of the detection sections ROI. In the pixels 103 in which the detection signal lines 112 pass, the conversion elements 104 and the detection signal lines 112 overlap with each other, and capacitances are formed in accordance with overlap areas. During irradiation with radiation, potentials of the detection signal lines 112 vary in accordance with variation of potentials of individual electrodes of the conversion elements 104 through the overlap capacitances, and a phenomenon of so-called crosstalk in which detection signals from the pixels 102 in the detection sections ROI vary occurs. Since a larger number of pixels 103 are arranged in the column direction when compared with the pixels 102 of the detection sections ROI, components of the crosstalk generated in the detection signal lines 112 is not negligible relative to the detection signals. It is difficult to totally avoid the crosstalk since parasitic capacitances generated due to spread of an electric field exist even in a case where the conversion elements 104 and the detection signal lines 112 do not two-dimensionally overlap with each other, for example. This is true to the dummy signal lines 1122 which are not connected to the pixels 102, and in the pixels 103 in which the dummy signal lines 1122 pass, capacitances are formed by the conversion elements 104 and the dummy signal lines 1122, and therefore, crosstalk is generated. Accordingly, crosstalk components in the detection signals output from the pixels 102 of the detection sections ROI obtained through the detection signal lines 112 may be corrected based on signals output from the dummy signal lines 1122. Specifically, if differences between the signals supplied from the detection signal lines 112 and the signals supplied from the dummy signal lines 1122 are obtained, the crosstalk components may be removed and the detection signals output from the pixels 102 of the detection sections ROI may be obtained. If the correction is performed using the dummy signal lines 1122 arranged in the vicinity of the detection signal lines 112 serving as correction targets, a more excellent effect may be attained. For example, a signal supplied from the detection signal line 112 (D3) may be corrected using a signal supplied from the dummy signal lines 1122 (D4).

In this embodiment, the detection signal lines 112 and the dummy signal lines 1122 are arranged at even intervals in the individual exposure regions ShotA. Furthermore, unlike the first embodiment described above, the detection signal lines 112 and the dummy signal lines 1122 are arranged at even intervals also in the exposure region groups 113.

Third Embodiment

Figure 10:
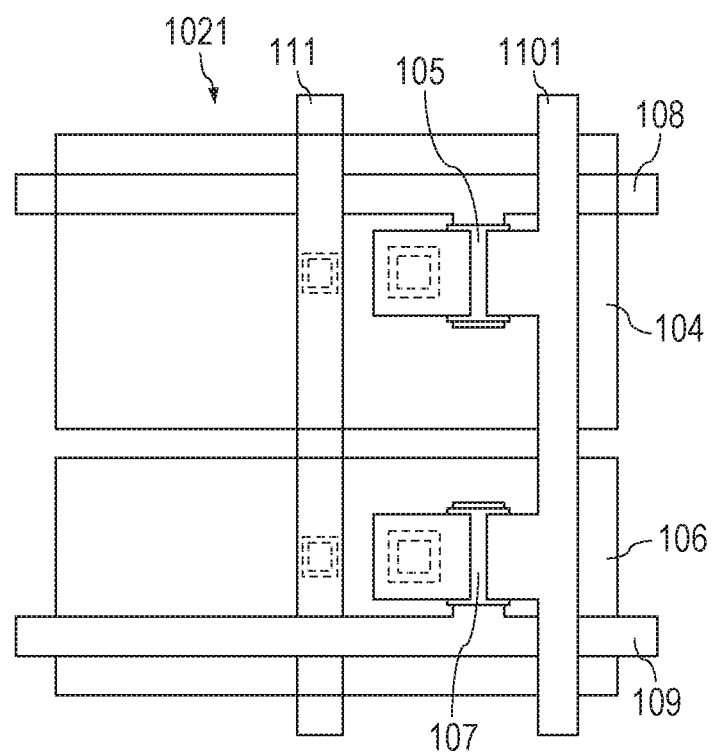
FIG. 10 is a plan view of a pixel for detecting a radiation amount included in a radiation imaging apparatus according to a third embodiment.

A radiation imaging apparatus according to a third embodiment will be described with reference to FIGS. 10 to 12C. FIG. 10 is a diagram illustrating a pixel 1021 for detecting an amount of incident radiation during irradiation with radiation according to the third embodiment. A conversion element 106 of the pixel 1021 is not connected to a dedicated one of detection signal lines 112 through a switch element 107 but connected to a detection signal line 1101 serving as an image signal line to which a signal is output from a conversion element 104 of a pixel 101. Specifically, the pixel 1021 is different from the pixels 102 described above in that the conversion element 104 for capturing a radiation image and the conversion element 106 for detecting a radiation amount share a signal line used to output signals. Furthermore, as illustrated in FIG. 12B, two detection sections ROI are arranged in each of the exposure regions ShotA in the radiation imaging apparatus 1100 of this embodiment. Other configurations of the radiation imaging apparatus 1100 may be the same as those of the radiation imaging apparatuses 100 and 800.

Figure 11:
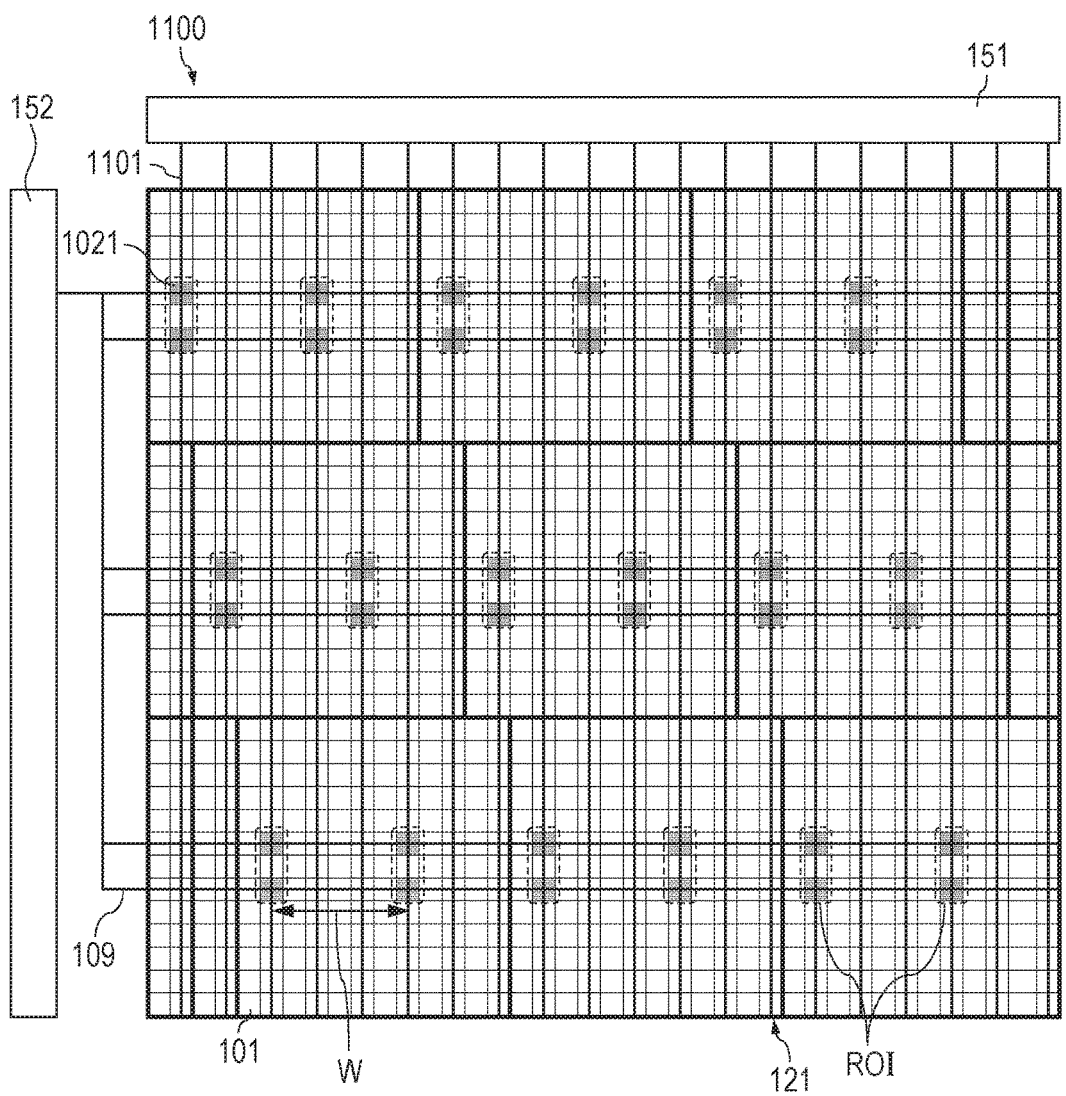
FIG. 11 is a diagram schematically illustrating layout of a configuration of the radiation imaging apparatus of FIG. 10.

FIG. 11 is a diagram schematically illustrating layout of a circuit configuration of the radiation imaging apparatus 1100 according to the third embodiment. Also in FIG. 11, in the circuit configuration, pixels 101 and 1021 which are disposed in an imaging region 121, detection signal lines 1101, control lines 109, detection sections ROI, a reading unit 151, and a controller 152 are illustrated, and image signal lines 110 and control lines 108 are omitted for simplicity of the drawing. In the imaging region 121 of the radiation imaging apparatus 1100 illustrated in FIG. 11, pixels in a matrix of 36 rows by 40 columns are arranged, and detection sections ROI are arranged in 18 portions. Furthermore, two pixels 1021 are included in each of the detection sections ROI. Furthermore, the pixels 1021 in the detection sections ROI which are arranged adjacent to each other in the column direction are connected to different detection signal lines 1101.

Figure 12A:
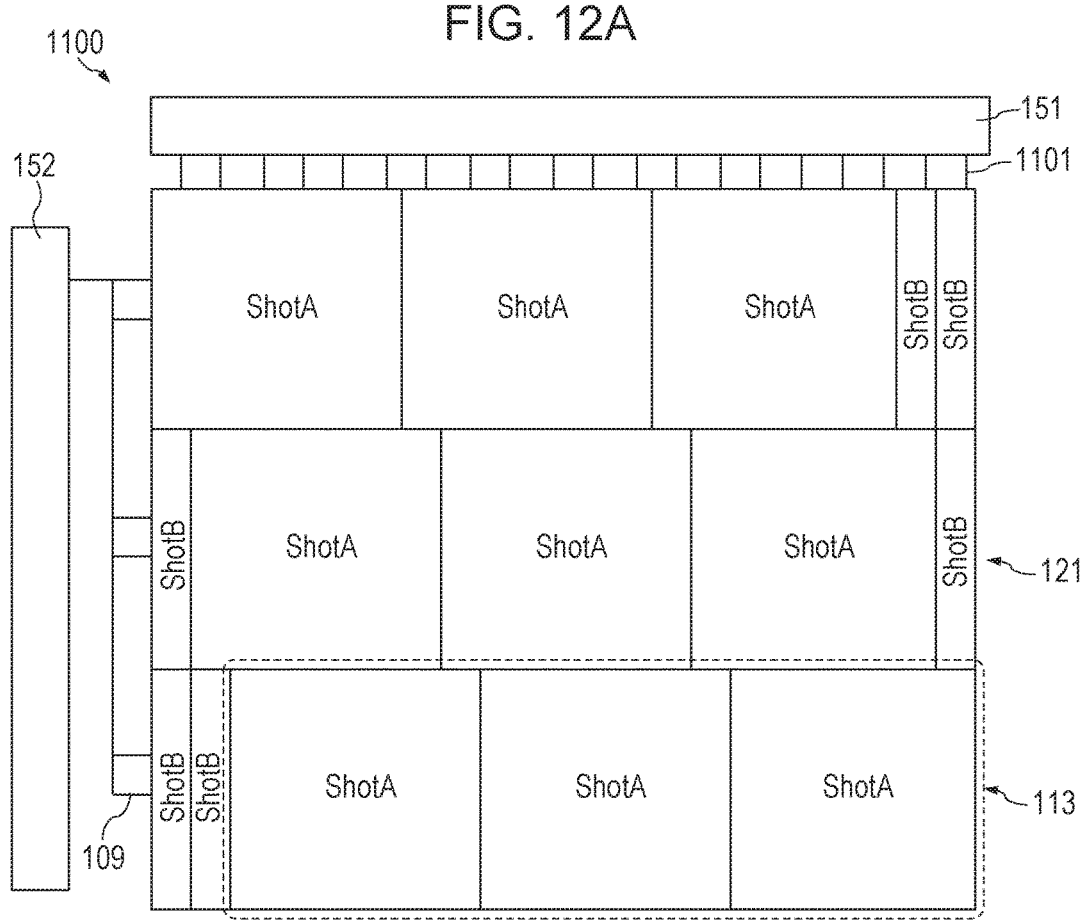
FIGS. 12A to 12C are diagrams illustrating an exposure region of the radiation imaging apparatus of FIG. 10.
Figure 12B:
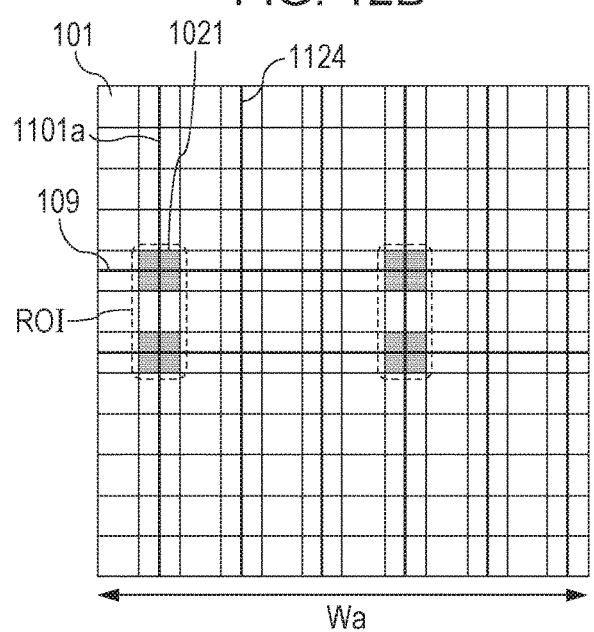
Figure 12C:
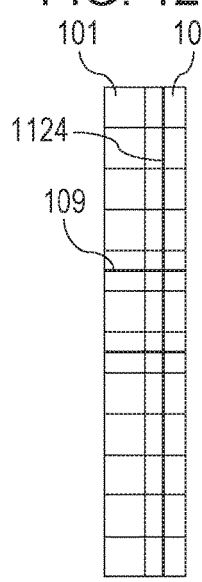

Next, a method for forming the imaging region 121 illustrated in FIG. 11 will be described with reference to FIGS. 12A to 12C. As illustrated in FIG. 12A, the imaging region 121 includes a plurality of exposure regions ShotA formed by exposure using the same mask pattern group. The imaging region 121 further includes a plurality of exposure regions ShotB formed by exposure using the same mask pattern which is different from that of the exposure regions ShotA. Therefore, components formed in the exposure regions ShotA correspondingly have the same configurations, and similarly, components formed in the exposure regions ShotB correspondingly have the same configurations. In this embodiment, an exposure region group 113 is formed by arranging three exposure regions ShotA in the row direction, and three exposure region groups 113 are arranged in the column direction. Therefore, the exposure region groups 113 have the same configuration. Furthermore, the six exposure regions ShotB are arranged. The components included in each of the exposure regions ShotA include, as illustrated in FIG. 12B, the pixels 101 and 1021, detection signal lines 1101a which serve as image signal lines as described above, which are part of the detection signal lines 1101, and which are connected to the pixels 1021 of the detection sections ROI, and the control lines 109. Furthermore, the components included in each of the exposure regions ShotA include signal lines 1124 which are part of the detection signal lines 1101 and which are connected to the detection signal lines 1101a of the other one of the exposure regions ShotA. The components included in each of the exposure regions ShotB include, as illustrated in FIG. 12C, the pixels 101, the control lines 109, and a signal line 1124. Also in this embodiment, any of the detection sections ROI including the pixels 102 are not included in the exposure regions ShotB. The image signal lines 110 and the control lines 108 are omitted also in FIGS. 12A to 12C for simplicity of the drawings.

In this embodiment, the detection signal lines 1101 which extend in the column direction are arranged every two pixels in a row direction as illustrated in FIG. 11. Furthermore, the exposure region groups 113 which are adjacent to each other in the column direction are shifted from each other in the row direction by an interval between the detection signal lines 1101 as illustrated in FIG. 12A using the exposure regions ShotB. By this, as illustrated in FIG. 11, the pixels 102 of the detection sections ROI included in the exposure region groups 113 which are arranged adjacent to each other in the column direction are connected to different detection signal lines 1101. Furthermore, also in this embodiment, similarly to a case of the exposure region groups 113 which are adjacent to each other in the column direction, the detection sections ROI which are disposed in different exposure region groups 113 are connected to different detection signal lines 1101. Accordingly, also in this embodiment, when a radiation image is captured while repeatability of pattern is realized for formation of pixels by exposing a pixel image, an operation of detecting an amount of radiation incident on the radiation imaging apparatus 1100 may be performed at high speed.

As a result, the detection sections ROI including the pixels 1021 are arranged at even intervals in the row direction of the exposure region groups 113. With this arrangement, assuming that a width of the exposure regions ShotA in the row direction is denoted by "Wa", an interval W between minimum units which include the pixels 1021 and which are repeatedly arranged is represented as follows: Wa=2 W. In a case where N minimum units are repeatedly arranged in each of the exposure regions ShotA, "Wa=N× W" is satisfied. Specifically, the interval W between the minimum units which include the respective pixels 1021 and which are repeatedly arranged is 1/integer of the width Wa of the exposure regions ShotA. A case where the pixels 102 or the pixels 1021 for detection of an amount of incident radiation in the exposure regions ShotA are not evenly arranged in the row direction will be described later.

In this embodiment, the detection signal lines 1101 are arranged at even intervals in the individual exposure regions ShotA. Similarly, the detection signal lines 1101 are evenly arranged also in the exposure region groups 113.

Fourth Embodiment

Figure 13:
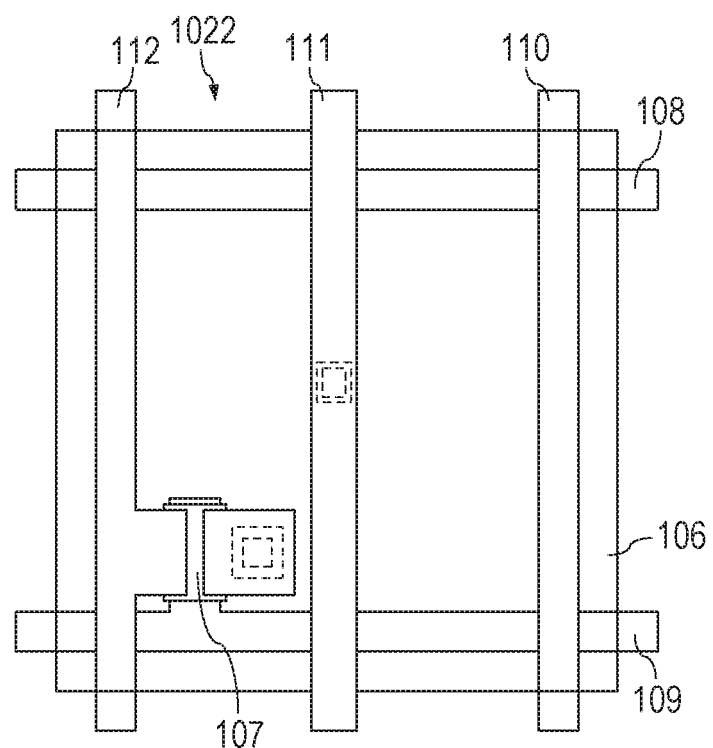
FIG. 13 is a plan view of a pixel for detecting a radiation amount included in a radiation imaging apparatus according to a fourth embodiment.

A radiation imaging apparatus according to a fourth embodiment will be described with reference to FIGS. 13 to 15C. FIG. 13 is a diagram illustrating a pixel 1022 for detection of an amount of incident radiation during irradiation with radiation according to the fourth embodiment. The pixel 1022 is different from the pixels 102 and 1021 described above in that the pixel 1022 includes a conversion element 106 for detection of an amount of incident radiation and a switching element 107 but does not include the conversion element 104 and the switch element 105 for imaging of a radiation image. When compared with the pixels 102 and 1021, a large area of the conversion element 106 is realized, and therefore, a large number of signals may be output, and accuracy of detection of a radiation amount may be improved even if an amount of incident radiation is small. Since the pixel 1022 does not have the conversion element 104 for imaging of a radiation image, pixel defect is included in a radiation image obtained in an imaging region 121. However, the radiation image may be corrected using signals output from pixels 101 and 103 which are positioned adjacent to or in the vicinity of the pixel 1022, for example. Furthermore, as with the radiation imaging apparatus 1100 described above, two detection sections ROI are arranged in each of exposure regions ShotA in a radiation imaging apparatus 1400 of this embodiment as illustrated in FIG. 15B. Other configurations of the radiation imaging apparatus 1400 may be the same as those of the radiation imaging apparatuses 100, 800, and 1100.

Figure 14:
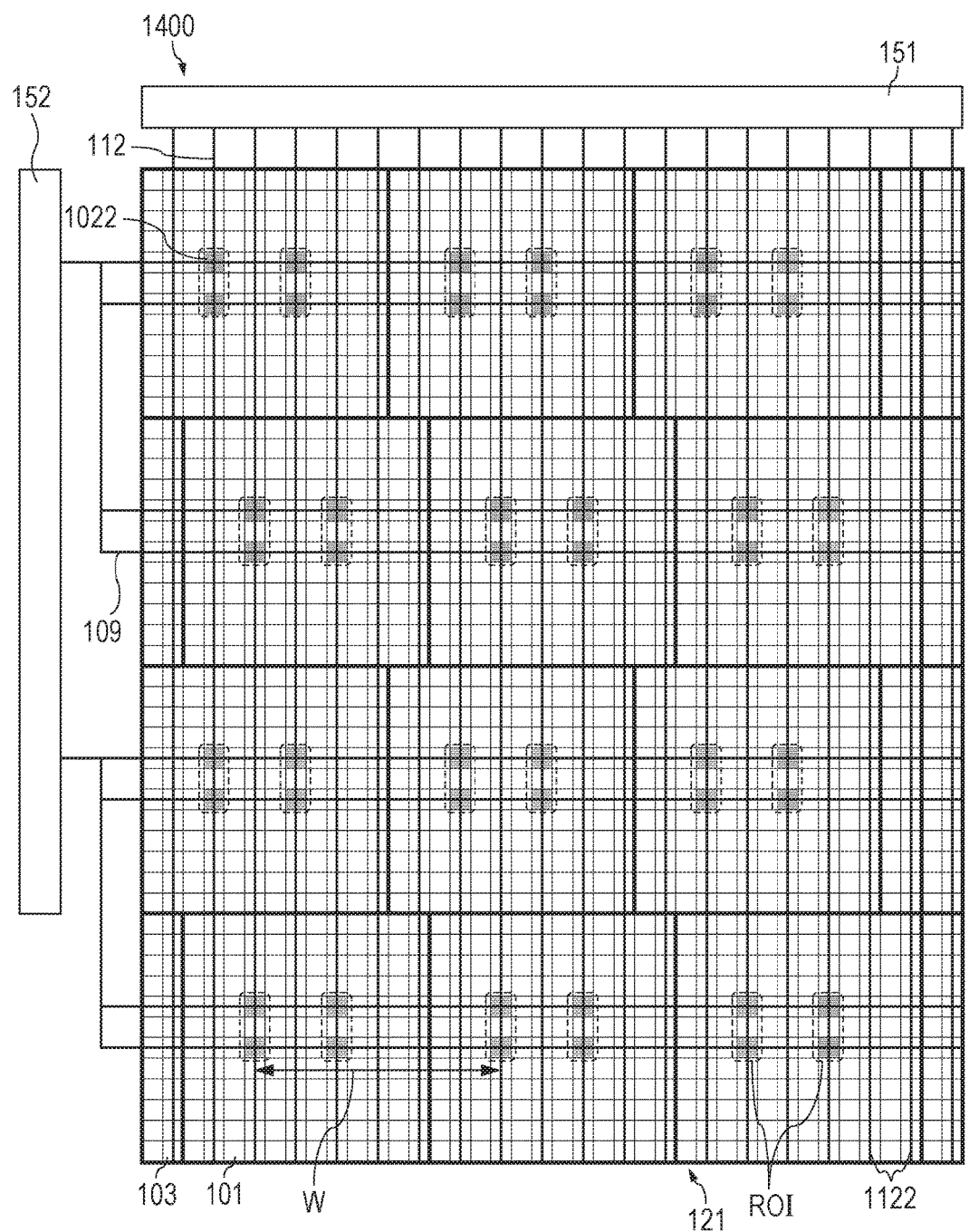
FIG. 14 is a diagram schematically illustrating layout of a configuration of the radiation imaging apparatus of FIG. 13.

FIG. 14 is a diagram schematically illustrating layout of a circuit configuration of a radiation imaging apparatus 1400 according to the fourth embodiment. Also in FIG. 14, in components in the circuit configuration, pixels 101, 1022, and 103 which are disposed in an imaging region 121, detection signal lines 112, dummy signal lines 1122, a control line 109, the detection sections ROI, a reading unit 151, and a controller 152 are illustrated. Furthermore, image signal lines 110 the control lines 108 are omitted for simplicity of the drawing. In the imaging region 121 of the radiation imaging apparatus 1400 illustrated in FIG. 14, pixels in a matrix of 48 rows by 38 columns are arranged, and detection sections ROI are arranged in 24 portions. Furthermore, two pixels 1022 are arranged in each of the detection sections ROI. Furthermore, also in this embodiment, the pixels 1022 in the detection sections ROI which are arranged adjacent to each other in a column direction are connected to different detection signal lines 112.

Figure 15A:
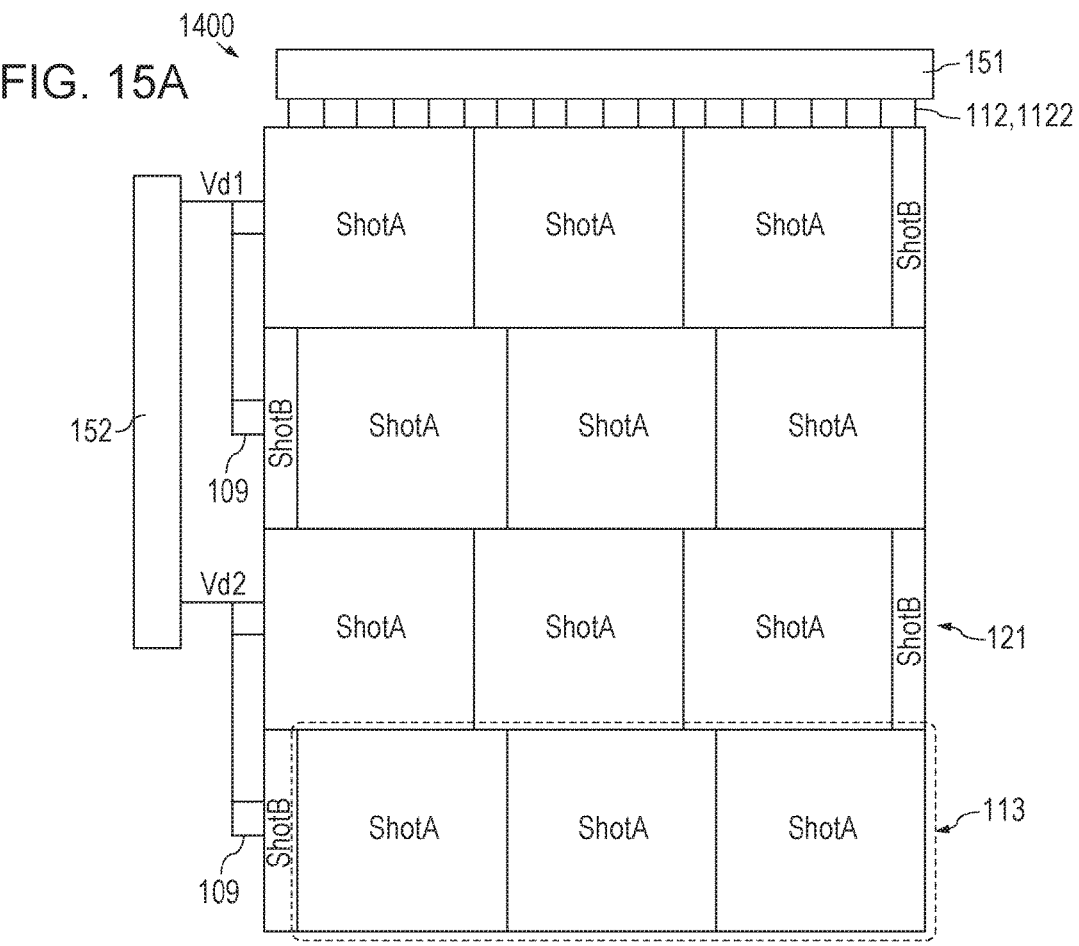
FIGS. 15A to 15C are diagrams illustrating an exposure region of the radiation imaging apparatus of FIG. 13.
Figure 15B:
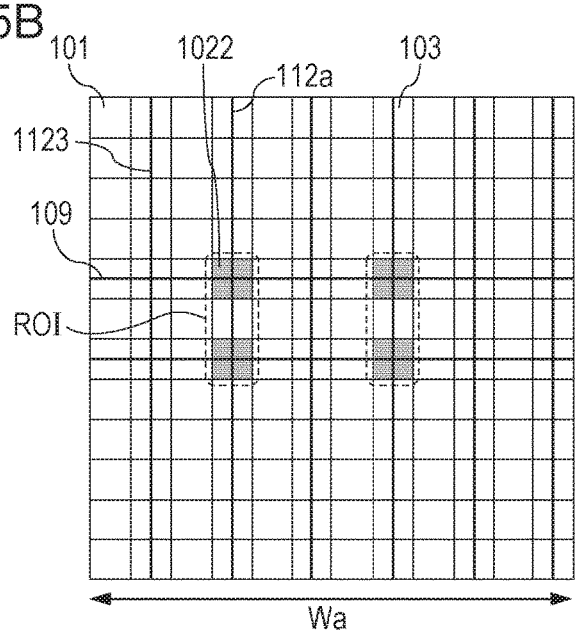
Figure 15C:
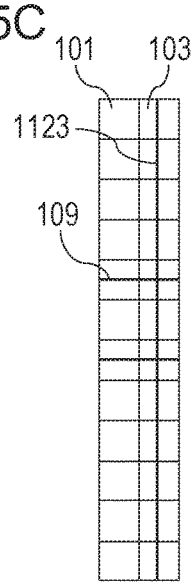

Next, a method for forming the imaging region 121 illustrated in FIG. 14 will be described with reference to FIGS. 15A to 15C. As illustrated in FIG. 15A, the imaging region 121 includes a plurality of exposure regions ShotA formed by exposure using the same mask pattern group. The imaging region 121 further includes a plurality of exposure regions ShotB formed by exposure using the same mask pattern which is different from that of the exposure regions ShotA. Therefore, components formed in the exposure regions ShotA correspondingly have the same configurations, and similarly, components formed in the exposure regions ShotB correspondingly have the same configurations. In this embodiment, an exposure region group 113 is formed by arranging three exposure regions ShotA in the row direction, and four exposure region groups 113 are arranged in the column direction. Therefore, the exposure region groups 113 have the same configuration. Furthermore, four exposure regions ShotB are arranged. The components included in each of the exposure regions ShotA include, as illustrated in FIG. 15B, the pixels 101, 1022, and 103, detection signal lines 112a which are part of corresponding detection signal lines 112 and which are connected to the corresponding pixels 1022 of the corresponding detection sections ROI, and the control lines 109. Furthermore, the components included in each of the exposure regions ShotA include signal lines 1123 which are connected to detection signal lines 112a of others of the exposure regions ShotA and which are part of the corresponding detection signal lines 112 or which are part of the corresponding dummy signal lines 1122. The components included in each of the exposure regions ShotB include, as illustrated in FIG. 15C, the pixels 101, the control lines 109, and a signal line 1123. Any of the detection sections ROI including the pixels 1022 are not included in the exposure regions ShotB. The image signal lines 110 and the control lines 108 are omitted also in FIGS. 15A to 15C for simplicity of the drawings.

In this embodiment, the detection signal lines 112 and the dummy signal lines 1122 which extend in the column direction are arranged every two pixels in a row direction as illustrated in FIG. 14. Furthermore, the exposure region groups 113 which are adjacent to each other in the column direction are shifted from each other in the row direction as illustrated in FIG. 15A using the exposure regions ShotB by an interval between the detection signal lines 112 and between the dummy signal lines 1122. By this, the pixels 1022 of the detection sections ROI included in the exposure region groups 113 which are arranged adjacent to each other in the column direction are connected to different detection signal lines 112. Furthermore, in this embodiment, among the four exposure region groups 113 arranged in the row direction, the pixels 1022 of the detection sections ROI in the exposure region groups 113 arranged in the uppermost portion and the corresponding pixels 1022 of the detection sections ROI in the exposure region groups 113 arranged in the third uppermost portion are connected to the same detection signal lines 112, and the pixels 1022 of the detection sections ROI in the exposure region groups 113 arranged in the second uppermost portion and the corresponding pixels 1022 of the detection sections ROI in the exposure region groups 113 arranged in the lowermost portion are connected to the same detection signal lines 112. Therefore, in a case where a signal Vd is simultaneously applied to the control lines 109 which control the exposure region groups 113 arranged in the uppermost portion and the second uppermost portion and the control lines 109 which control the exposure region groups 113 arranged in the third uppermost portion and the lowermost portion, signals of different detection sections ROI are mixed. Therefore, as illustrated in FIG. 15A, an ON voltage is successively applied to a signal Vd1 corresponding to the control lines 109 which control the exposure region groups 113 arranged on an upper side and a signal Vd2 corresponding to the control lines 109 which control the exposure region groups 113 arranged on a lower side so that signals are read. Although a driving speed is lowered when compared with the foregoing embodiments, signals may be simultaneously read from a plurality of detection sections ROI also in this embodiment. Accordingly, even in this embodiment, when a radiation image is captured while repeatability of pattern is realized for formation of pixels by exposing a pixel image, an operation of detecting an amount of radiation incident on the radiation imaging apparatus 1400 may be performed at high speed.

As a result, the detection sections ROI including the pixels 1022 are arranged at uneven intervals in the row direction of the exposure region groups 113. With this arrangement, assuming that a width of the exposure regions ShotA is denoted by "Wa", an interval W between minimum units which include the pixels 1022 and which are repeatedly arranged is represented as follows: Wa=W. Specifically, the interval W between the minimum units which include the respective pixels 1022 and which are repeatedly arranged is equal to the width Wa of the exposure regions ShotA.

Although the conversion elements 106 are connected to the detection signal lines 112 through the switch elements 107 in this embodiment, the disclosure is not limited to this. The conversion elements 106 may be directly connected to the detection signal lines 112, for example.

In this embodiment, the detection signal lines 112 and the dummy signal lines 1122 are arranged at even intervals in the individual exposure regions ShotA. Furthermore, the detection signal lines 112 and the dummy signal lines 1122 are arranged at even intervals also in the exposure region groups 113.

The four embodiments have been described hereinabove. The disclosure is not limited to the embodiments, and various modifications and combinations may be made without departing from the scope of the disclosure.

Figure 16:
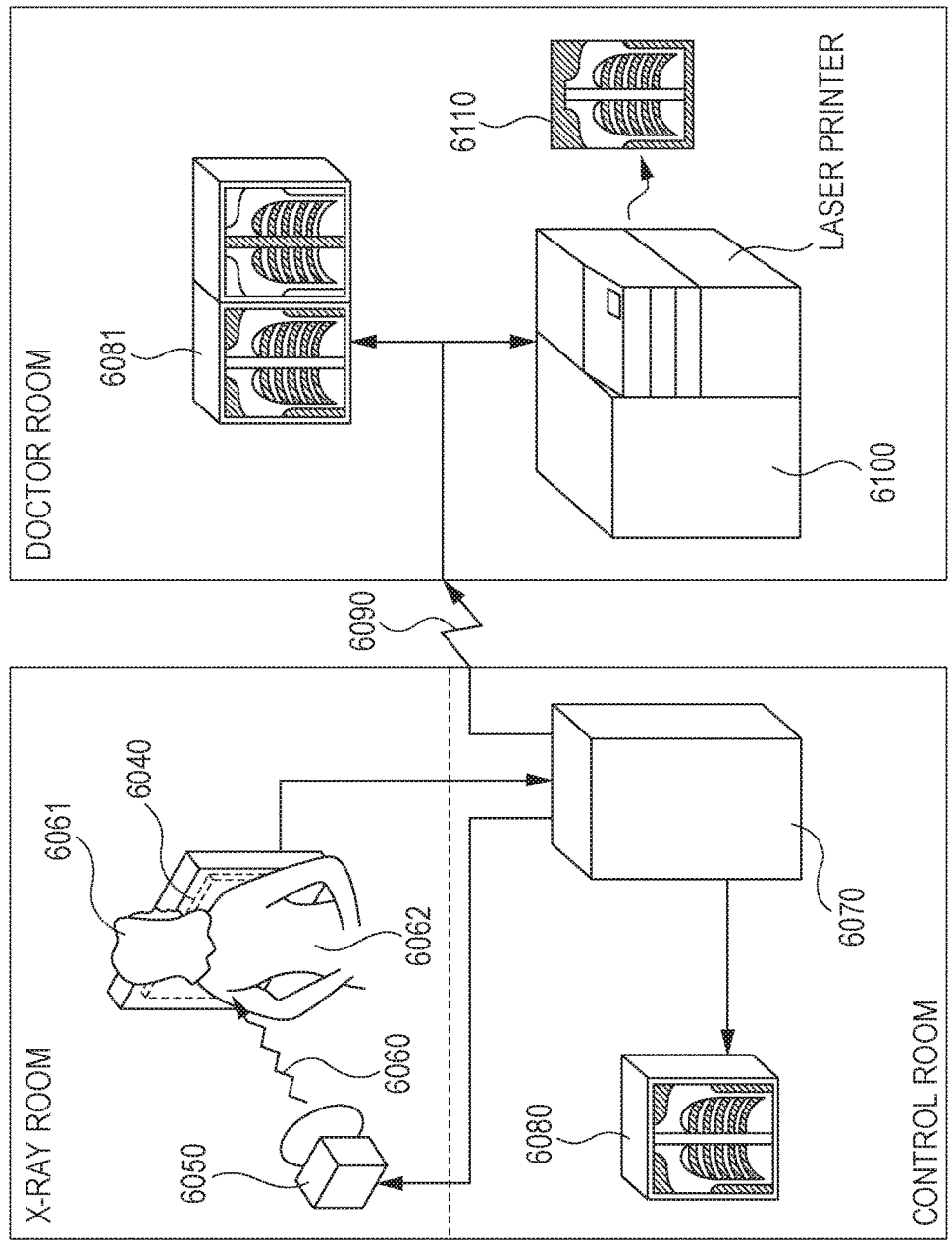
FIG. 16 is a diagram illustrating a configuration of a radiation imaging system employing one of the radiation imaging apparatuses according to the aspect of the embodiments.

A radiation imaging system incorporating the radiation imaging apparatus will be described with reference to FIG. 16. An X-ray 6060 generated in an X-ray tube 6050 serving as a radiation source is transmitted through a chest portion 6062 of a patient or an examiner 6061 and is incident on the radiation imaging apparatus of the aspect of the embodiments. The radiation imaging apparatus 6040 may be any one of the radiation imaging apparatuses 100, 800, 1100, and 1400. The incident X-ray includes information on an inside of a body of the patient or the examiner 6061. In the radiation imaging apparatus 6040, a scintillator emits light in response to the incident X-ray 6060, the light is subjected to photoelectric conversion by a photoelectric conversion element so that electric information is obtained. This information is converted into digital data, is subjected to image processing performed by an image processor 6070 serving as a signal processor, and may be observed by a display 6080 serving as a display unit in a control room. Furthermore, the information may be transferred to a remote location by a transmission processor, such as a network 6090 including a telephone, a local area network (LAN), and the Internet. In this way, the information may be displayed in a display 6081 serving as a display unit in another location, such as a doctor room, and a doctor in the remote location may make a diagnosis. Furthermore, the information may be recorded in a recording medium, such as an optical disc, or may be recorded in a film 6110 serving as a recording medium, using a film processor 6100.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2015-230695 filed Nov. 26, 2015, which is hereby incorporated by reference herein in its entirety.

What is claimed is:

1. An apparatus comprising:
a plurality of first groups having same configurations configured to be arranged in a row direction and a column direction, each of the first groups including a plurality of pixels for obtaining a radiation image and at least one detection section for detecting an amount of incident radiation;
one of a plurality of detection signal lines configured to connect to one of detection sections of the plurality of first groups; and
a second group having a plurality of pixels for obtaining a radiation, image and having a configuration different from each of the plurality of first groups,
wherein the second group is arranged in the row direction of one of two of the first groups which are arranged in the column direction, and the two of the first groups are shifted from each other in the row direction in accordance with a width of the second group in the row direction, and
wherein the detection sections included in the two of the first groups are connected to different detection signal lines in the plurality of detection signal lines.

2. The apparatus according to claim 1, wherein the second group does not include the detection section.

3. The apparatus according to claim 1,
wherein each of the plurality of first groups includes a plurality of sub-groups having same configuration and are arranged in the row direction, and
wherein each of the sub-groups includes some of the plurality of pixels included in the plurality of first groups and the detection section.

4. The apparatus according to claim 3, wherein, in each of the plurality of sub-groups, the plurality of detection signal lines are arranged at even intervals.

5. The apparatus according to claim 3, further comprising:
at least one dummy signal line which is not connected to any of the detection sections and a plurality of pixels included in the plurality of first groups and a plurality of second groups and which extends in the column direction, wherein the dummy signal line is connected to a reading unit which is connected to the plurality of detection signal lines and which processes signals output from the detection sections, and wherein the reading unit corrects the signals output from the detection sections in accordance with a signal output from the dummy signal line.

6. The apparatus according to claim 5, wherein, in each of the plurality of sub-groups, the plurality of detection signal lines and the dummy signal line are arranged at even intervals.

7. The apparatus according to claim 5, wherein, in each of the plurality of first groups, the plurality of detection signal lines and the dummy signal line are arranged at even intervals.

8. The apparatus according to claim 1, wherein, in each of the plurality of first groups, the plurality of detection signal lines are arranged at even intervals.

9. The apparatus according to claim 1, wherein some of a plurality of second groups are arranged in the row direction so as to be adjacent to at least one of opposite ends of one of the plurality of first groups in the row direction.

10. The apparatus according to claim 1, further comprising a plurality of image signal lines which receive signals output from the plurality of pixels and which extend in the column direction.

11. The apparatus according to claim 10, wherein one of the plurality of image signal lines is used as one of the plurality of detection signal lines.

12. The apparatus according to claim 1, wherein each of the detection sections includes at least one conversion element for detecting an amount of incident radiation which is connected to the same detection signal line among the plurality of detection signal lines.

13. A system comprising:
the radiation imaging apparatus according to claim 1; and
a signal processor configured to process signals supplied from the apparatus.

14. A method for an apparatus including a plurality of first groups having same configuration and arranged in a row direction and a column direction, each of the first groups including a plurality of pixels for obtaining a radiation image and at least one detection section for detecting an amount of incident radiation, and one of a plurality of detection signal lines connected to the detection sections of the plurality of first groups, the method comprising:
forming an imaging region including the plurality of first groups on a substrate such that two of the plurality of first groups which are arranged in the column direction are shifted from each other in the row direction by performing first exposure using a first mask pattern for forming the first groups and the detection sections included in the two of the plurality of first groups are connected to different detection signal lines in the plurality of detection signal lines, wherein some of a plurality of second groups configured differently from the plurality of first groups respectively are arranged in the row direction so as to be adjacent to at least one of opposite ends of one of the plurality of first groups in the row direction.

15. The method according to claim 14,
wherein each of the plurality of first groups includes a plurality of sub-groups having same configuration and are arranged in the row direction, and
wherein each of the sub-groups includes some of the plurality of pixels included in the plurality of first groups and the detection section.

16. The method according to claim 14, further comprising arranging the plurality of detection signal lines at even intervals in each of the plurality of first groups.

17. The method according to claim 14, further comprising a plurality of image signal lines which receive signals output from the plurality of pixels and which extend in the column direction.

18. The method according to claim 14, wherein each of the detection sections includes at least one conversion element for detecting an amount of incident radiation which is connected to the same detection signal line among the plurality of detection signal lines.

19. A method for an apparatus including a plurality of first groups having same configuration and arranged in a row direction and a column direction, each of the first groups including a plurality of pixels for obtaining a radiation image and at least one detection section for detecting an amount of incident radiation, and one of a plurality of detection signal lines connected to one of detection sections of the plurality of first groups, the method comprising:
forming an imaging region including the plurality of first groups on a substrate such that two of the plurality of first groups which are arranged in the column direction are shifted from each other in the row direction by performing first exposure using a first mask pattern for forming the first groups and the detection sections included in the two of the plurality of first groups are connected to different detection signal lines in the plurality of detection signal lines,
wherein, in the forming, an imaging region including the plurality of first groups and a second group is formed on the substrate such that the second group is arranged in the row direction of one of the two groups by performing second exposure, which is different from the first exposure, using a second mask pattern for forming the second group having a configuration different from that of the plurality of first groups, the two groups are shifted in the row direction in accordance with a width of the second group in the row direction, and the detection sections included in the two groups are connected to different detection signal lines in the plurality of detection signal lines.

* * * * *